(12) United States Patent
Gifford, III et al.

(10) Patent No.: US 6,712,842 B1
(45) Date of Patent: *Mar. 30, 2004

(54) METHODS AND DEVICES FOR LINING A BLOOD VESSEL AND OPENING A NARROWED REGION OF A BLOOD VESSEL

(75) Inventors: Hanson S. Gifford, III, Woodside, CA (US); Ivan Sepetka, Los Altos, CA (US); Mark E. Deem, Mountain View, CA (US); Douglas S. Sutton, Pacifica, CA (US); Allan R. Will, Atherton, CA (US); Martin S. Dieck, Cupertino, CA (US); Sunmi Chew, San Jose, CA (US)

(73) Assignee: Allan Will, Atherton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/522,316

(22) Filed: Mar. 9, 2000

Related U.S. Application Data

(63) Continuation-in-part of application No. 09/416,309, filed on Oct. 12, 1999.

(51) Int. Cl.$^7$ .................................................. A61F 2/06
(52) U.S. Cl. ...................................... 623/1.13; 623/1.23
(58) Field of Search ........................... 623/1.13, 1.23, 623/1.36, 1.2; 604/506–509, 96.01; 606/108, 151–158, 198, 194

(56) References Cited

U.S. PATENT DOCUMENTS

| | | |
|---|---|---|
| 3,657,744 A | 4/1972 | Ersek |
| 3,868,956 A | 3/1975 | Alfidi et al. |
| 3,945,052 A | 3/1976 | Liebig |
| 4,140,126 A | 2/1979 | Choudhury |
| 4,550,447 A | 11/1985 | Seiler, Jr. et al. |
| 4,562,596 A | 1/1986 | Kornberg |
| 4,649,922 A | 3/1987 | Wiktor |
| 4,681,110 A | 7/1987 | Wiktor |
| 4,728,328 A | 3/1988 | Hughes et al. |
| 4,732,152 A | * 3/1988 | Wallsten et al. ........... 623/1.11 |
| 4,740,207 A | 4/1988 | Kreamer |
| 4,743,251 A | 5/1988 | Barra |
| 4,787,899 A | 11/1988 | Lazarus |
| 4,820,298 A | 4/1989 | Leveen et al. |
| 4,878,906 A | 11/1989 | Lindemann et al. |
| 4,957,508 A | 9/1990 | Kaneko et al. |

(List continued on next page.)

FOREIGN PATENT DOCUMENTS

| | | |
|---|---|---|
| WO | WO 97/03717 | 2/1997 |
| WO | WO 97/19653 | 6/1997 |
| WO | WO 98/04212 | 2/1998 |
| WO | WO 98/07389 | 2/1998 |
| WO | WO 98/41167 | 9/1998 |
| WO | WO 99/37244 | 7/1999 |
| WO | WO 99/48440 | 9/1999 |

OTHER PUBLICATIONS

Dotter et al., "Transluminal Expandable Nitinol Coil Stent Grafting: Preliminary Report," *Radiology*, 147, pp. 259–260 (Apr. 1983).

Cragg et al., "Nonsurgical Placement of Arterial Endoprostheses: A New Technique Using Nitinol Wire," *Radiology*, 147, pp. 261–263 (Apr. 1983).

(List continued on next page.)

*Primary Examiner*—Michael J. Milano
*Assistant Examiner*—Jason R Baxter
(74) *Attorney, Agent, or Firm*—Jens E. Hoekendijk; Hoekendijk & Lynch, LLP

(57) ABSTRACT

A liner is advanced through a narrowed region in a vessel such as the internal carotid artery. The liner is advanced through the narrowed region in a collapsed position. A stent is then advanced through the liner and expanded to open the narrowed region. The liner may also have an anchor which expands an end of the liner before the stent is introduced.

88 Claims, 36 Drawing Sheets

U.S. PATENT DOCUMENTS

| | | | |
|---|---|---|---|
| 5,078,726 A | 1/1992 | Kreamer | |
| 5,104,399 A | 4/1992 | Lazarus | |
| 5,123,917 A | 6/1992 | Lee | |
| 5,137,512 A | 8/1992 | Burns et al. | |
| 5,151,105 A | 9/1992 | Kwan-Gett | |
| 5,211,658 A | 5/1993 | Clouse | |
| 5,219,355 A | 6/1993 | Parodi et al. | |
| 5,275,622 A | 1/1994 | Lazarus et al. | |
| 5,360,443 A | 11/1994 | Barone et al. | |
| 5,366,473 A | 11/1994 | Winston et al. | |
| 5,443,499 A | 8/1995 | Schmitt | |
| 5,456,694 A * | 10/1995 | Marin et al. | 623/1.13 |
| 5,456,713 A | 10/1995 | Chuter | |
| 5,489,295 A * | 2/1996 | Piplani et al. | 606/153 |
| 5,510,077 A | 4/1996 | Dinh et al. | |
| 5,554,183 A | 9/1996 | Nazari | |
| 5,556,414 A | 9/1996 | Turi | |
| 5,571,171 A | 11/1996 | Barone et al. | |
| 5,578,071 A | 11/1996 | Parodi | |
| 5,591,195 A | 1/1997 | Taheri et al. | |
| 5,591,226 A | 1/1997 | Trerotola et al. | |
| 5,609,628 A | 3/1997 | Keranen | |
| 5,617,878 A | 4/1997 | Taheri | |
| 5,647,857 A | 7/1997 | Anderson et al. | |
| 5,662,702 A | 9/1997 | Keranen | |
| 5,666,969 A * | 9/1997 | Urick et al. | 600/434 |
| 5,693,087 A | 12/1997 | Parodi | |
| 5,695,499 A | 12/1997 | Helgerson et al. | |
| 5,697,380 A * | 12/1997 | Quiachon et al. | 604/531 |
| 5,713,907 A | 2/1998 | Hogendijk et al. | |
| 5,713,917 A | 2/1998 | Leonhardt et al. | |
| 5,713,948 A | 2/1998 | Uflacker | |
| 5,728,131 A | 3/1998 | Frantzen et al. | |
| 5,749,918 A | 5/1998 | Hogendijk et al. | |
| 5,749,920 A | 5/1998 | Quiachon et al. | |
| 5,769,882 A | 6/1998 | Fogarty et al. | |
| 5,769,887 A | 6/1998 | Brown et al. | |
| 5,772,669 A | 6/1998 | Vrba | |
| 5,776,186 A | 7/1998 | Uflacker | |
| 5,782,906 A | 7/1998 | Marshall et al. | |
| 5,785,679 A | 7/1998 | Abolfahti et al. | |
| 5,800,521 A | 9/1998 | Orth | |
| 5,800,522 A | 9/1998 | Campbell et al. | |
| 5,807,327 A | 9/1998 | Green et al. | |
| 5,824,040 A | 10/1998 | Cox et al. | |
| 5,824,052 A | 10/1998 | Khosravi et al. | |
| 5,824,053 A | 10/1998 | Khosravi et al. | |
| 5,824,054 A | 10/1998 | Khosravi et al. | |
| 5,824,055 A | 10/1998 | Spiridigliozzi et al. | |
| 5,843,089 A | 12/1998 | Sahatjian et al. | |
| 5,849,034 A | 12/1998 | Schwartz | |
| 5,860,998 A | 1/1999 | Robinson et al. | |
| 5,873,905 A | 2/1999 | Plaia et al. | |
| 5,916,263 A | 6/1999 | Goicoechea et al. | |
| 5,925,063 A | 7/1999 | Khosravi | |
| 5,928,279 A | 7/1999 | Shannon et al. | |
| 5,935,161 A | 8/1999 | Robinson et al. | |
| 5,938,696 A | 8/1999 | Goicoechea et al. | |
| 5,941,908 A | 8/1999 | Goldsteen et al. | |
| 5,948,017 A | 9/1999 | Taheri | |
| 5,948,191 A | 9/1999 | Solovay | |
| 5,957,973 A | 9/1999 | Quiachon et al. | |
| 5,957,974 A | 9/1999 | Thompson et al. | |
| 5,961,545 A | 10/1999 | Lentz et al. | |
| 5,968,069 A * | 10/1999 | Dusbabek et al. | 606/194 |
| 5,993,489 A | 11/1999 | Lewis et al. | |
| 6,007,573 A | 12/1999 | Wallace et al. | |
| 6,015,429 A | 1/2000 | Lau et al. | |
| 6,015,430 A | 1/2000 | Wall | |
| 6,017,362 A | 1/2000 | Lau | |
| 6,030,407 A | 2/2000 | Eidenschink | |
| 6,123,723 A * | 9/2000 | Konya et al. | 623/1.11 |
| 6,132,457 A | 10/2000 | Chobotov | |
| 6,139,540 A | 10/2000 | Rost et al. | |
| 6,319,275 B1 * | 11/2001 | Lashinski et al. | 606/108 |
| 6,383,171 B1 * | 5/2002 | Gifford et al. | 623/1.13 |

OTHER PUBLICATIONS

Cragg et al., "Percutaneous Arterial Grafting," *Radiology*, 147, pp. 45–49 (1984).

Mass et al., "Radiological Follow–up of Transluminally Inserted Vascular Endoprostheses: An Experimental Study Using Expanding Spirals," *Radiology*, 152, pp. 659–663, (1984).

Palmaz, et al., "Expandable intraluminal vascular graft: A feasibiliety study," *Surgery*, 90:2, pp. 199–205 (Feb. 1986).

Lawrence, et al., "Percutaneous Endovascular Graft: Experimental Evaluation," *Radiology*, 163, pp. 357–360 (1987).

Matsumae et al., "An experimental study of a new sutureless intraluminal graft with an elastic ring that can attach itself to the vessel wall," *J. Vascular Surg.*, pp. 38–44 (Jul. 1988).

Mirich et al., "Percutaneously Placed Endovascular Grafts for Aortic Aneurysms: Feasibility Study," *Radiology*, 170, pp. 1033–1037 (Mar. 1989).

* cited by examiner

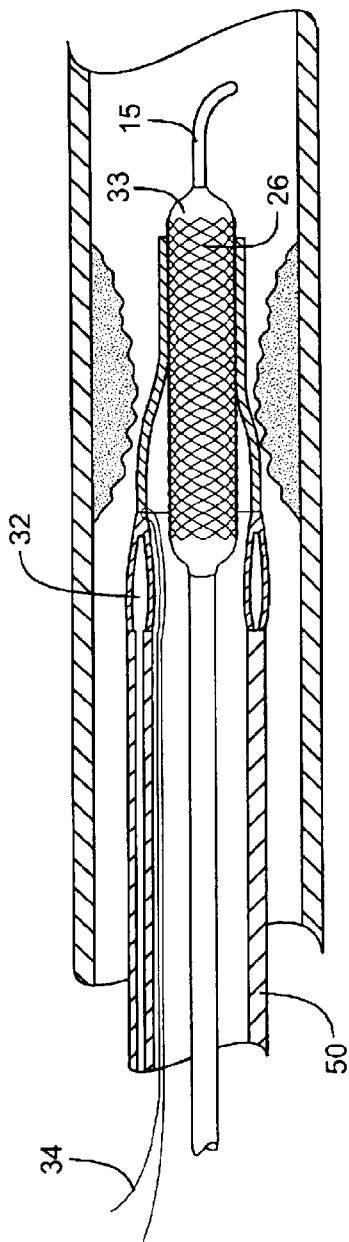
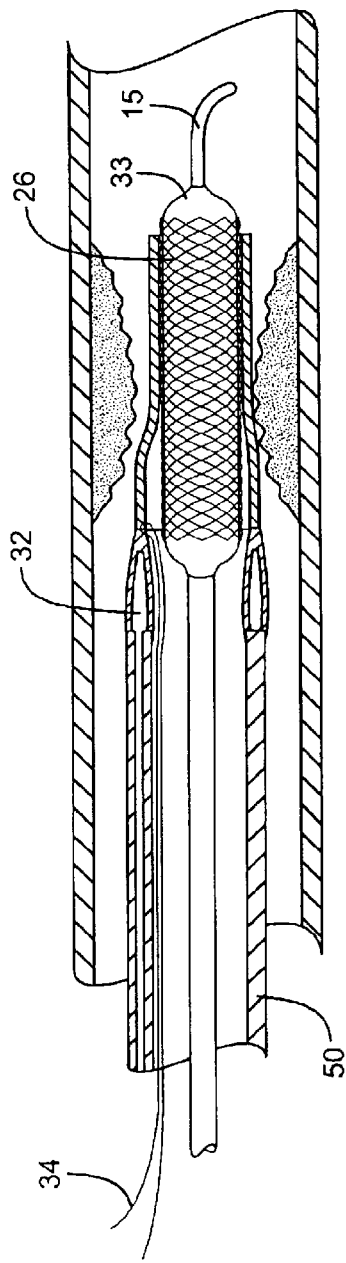
FIG. 36
FIG. 37

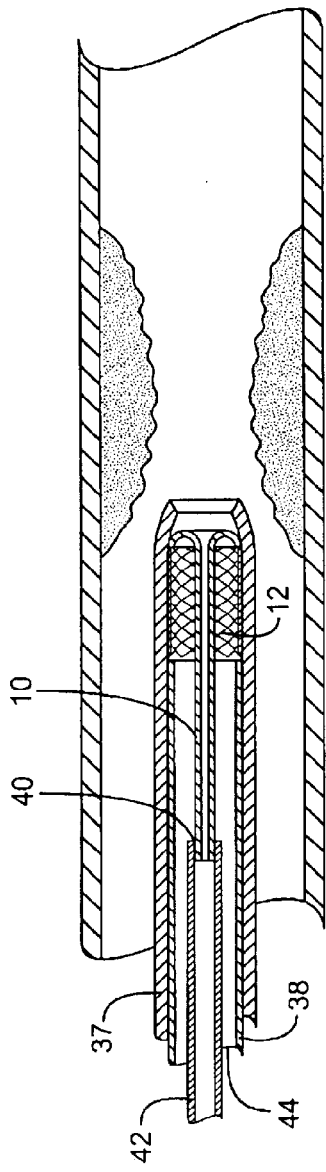
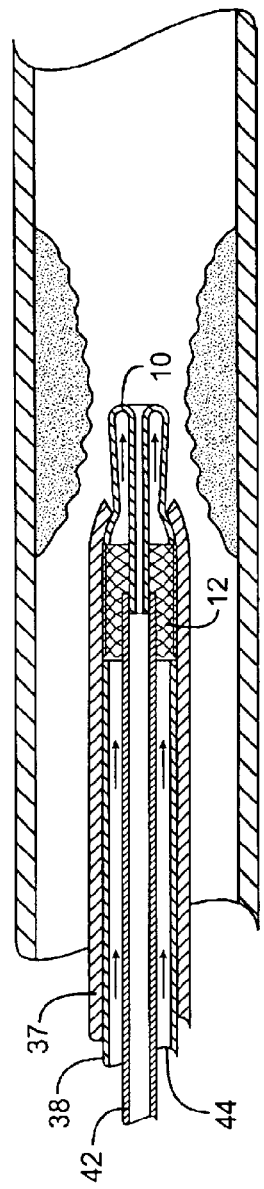
FIG. 41
FIG. 42

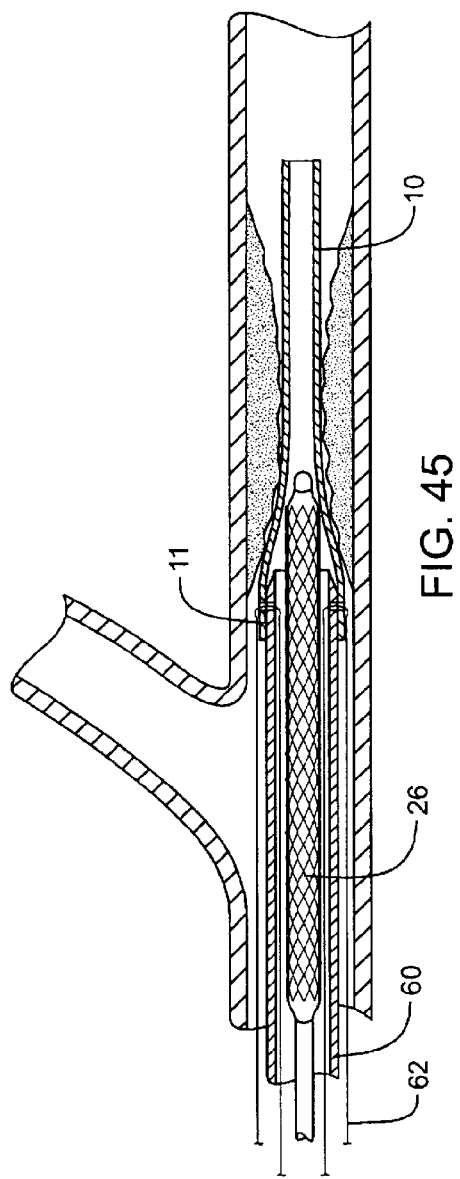
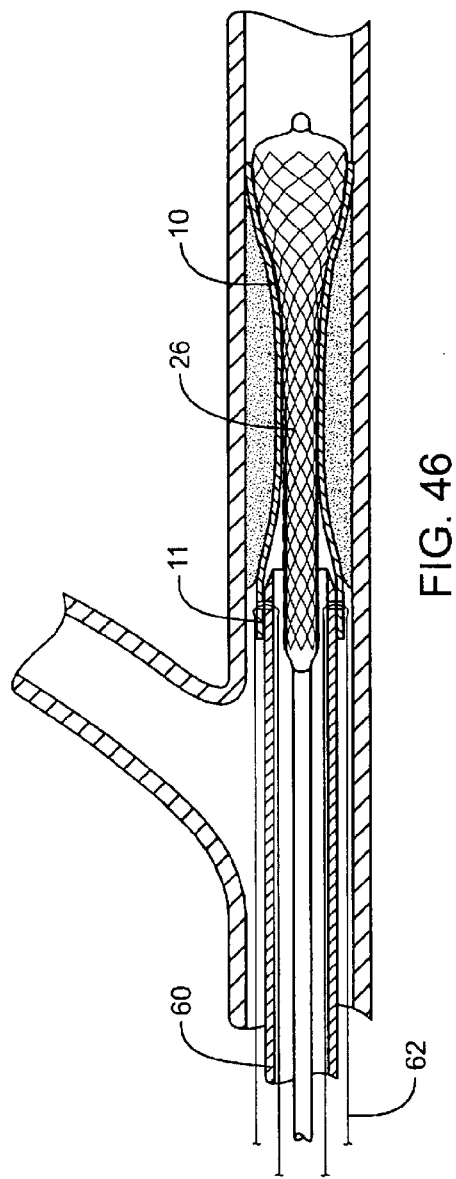
FIG. 45
FIG. 46

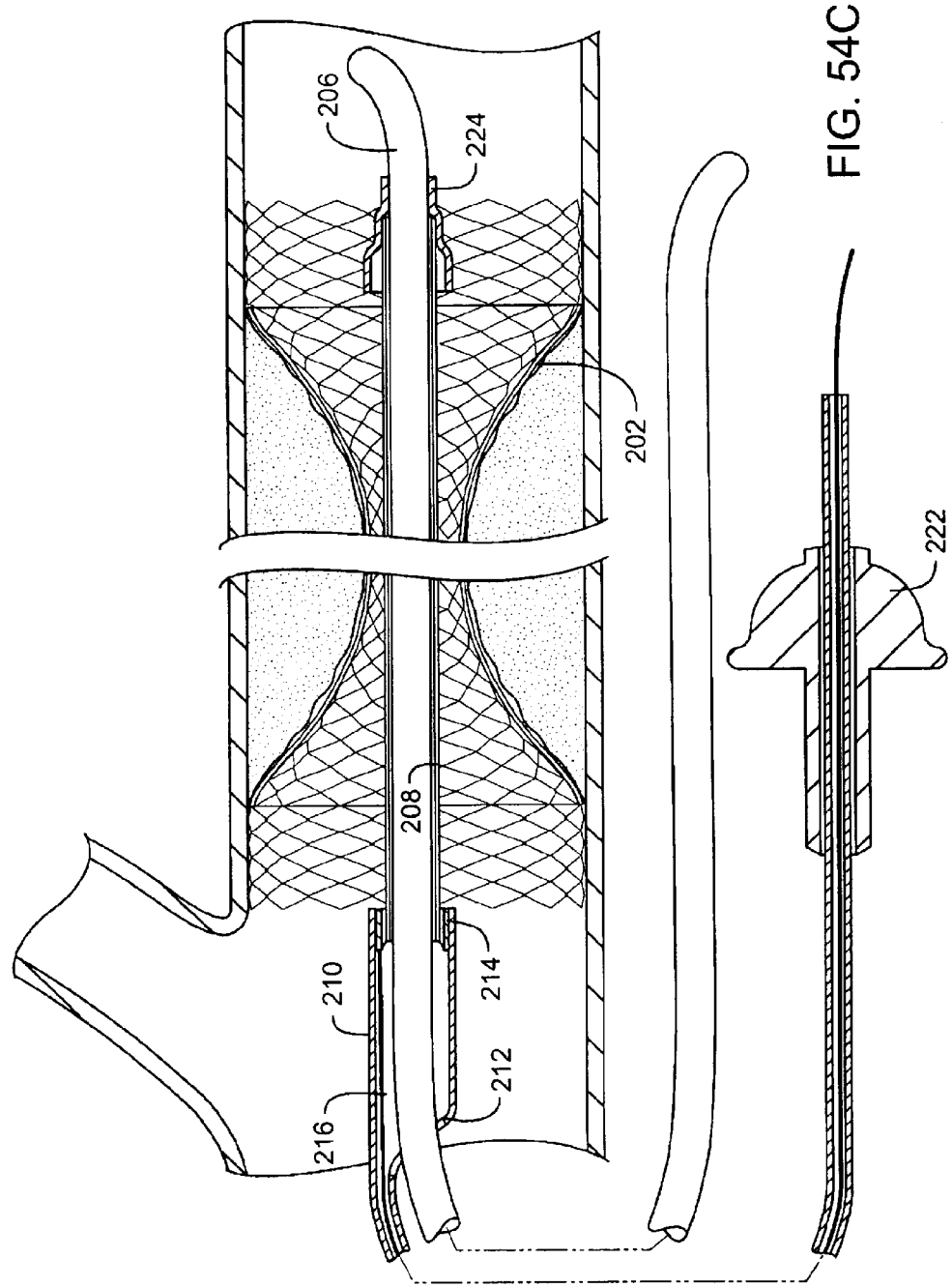

METHODS AND DEVICES FOR LINING A BLOOD VESSEL AND OPENING A NARROWED REGION OF A BLOOD VESSEL

CROSS-REFERENCE TO RELATED APPLICATION

This application is a continuation-in-part of 09/416,309, filed Oct. 12, 1999, which is hereby incorporated by reference.

BACKGROUND OF THE INVENTION

The present invention is directed to methods and devices for protecting a passageway in a body when advancing devices through the passageway. A specific application of the present invention is for treatment of blood vessels although the invention may be used in any part of the body. For example, the present invention is used to protect blood vessels during intravascular procedures for treating aneurysms, arteriovenous malformations, and atherosclerotic disease of vessels. A particular application of the present invention is for atherosclerotic disease of the carotid arteries or saphenous vein grafts. Carotid artery atherosclerotic occlusive disease contributes to hundreds of thousands of strokes annually in the United States. Atherosclerotic disease of the internal carotid artery is particularly problematic since plaque from the internal carotid artery leads directly to the cerebral vasculature.

A conventional method of treating carotid artery occlusive disease is by surgical removal of the plaque (carotid endarterectomy). The carotid artery is opened surgically, the plaque is removed and the carotid artery is then closed. Carotid endarterectomies have demonstrated significant clinical benefit over conservative treatment with medication by reducing strokes over the next five years. Although carotid endarteretomy reduces strokes over a period of time after the procedure, the procedure still has a 6% risk of death or stroke.

Another method of treating carotid artery disease is to use interventional devices such as stents. A problem with treating carotid artery occlusive disease with stents is that the user is wary of dislodging plaque when advancing the stent through the carotid artery. Any plaque which breaks free during introduction of the stent travels directly to the patient's brain and can cause a stroke or death.

Yet another method of treating carotid artery occlusive disease is to introduce a filter through the carotid artery to trap emboli released during subsequent deployment of a stent or angioplasty balloon. This method suffers the same drawback in that advancement of the filter itself may dislodge plaque. Moreover, exchange of various therapeutic catheters over the filter element result in undesirable movement of the filter with attendant risk of losing filtered emboli or damaging the vessel wall with the filter.

The present invention is directed to improved methods of protecting a body passageway when advancing devices through the body passageway. The present invention is also directed to improved methods of treating atherosclerotic vessels and, in particular, occlusive disease of the internal carotid artery.

SUMMARY OF THE INVENTION

In accordance with the objects of the invention, a liner is provided to protect a body passageway during introduction of other devices into the passageway. In a specific application, the methods and devices of the present invention are used to protect blood vessels, such as the internal carotid artery, during intravascular procedures. It is understood that use of the present invention for protection of blood vessels is discussed as an example of how the present invention may be used, however, the invention may be used in any other part of the body without departing from the scope of the invention. The liner is collapsed for introduction into the patient and advanced to a narrowed region of a blood vessel. The liner is passed through a region of the blood vessel in the collapsed condition and an intravascular device, such as a stent or filter, is then introduced into the liner. The liner may be used to protect vessels from any type of problem including atherosclerotic disease, perforation, aneurysm or AVM.

The liner protects the vessel as the intravascular device is passed through the region to prevent the device from dislodging plaque. When the device is a stent, the stent is preferably expanded within the liner to trap the liner between the stent and the vessel. The liner may be expanded by the stent or may be partially or fully expanded before introduction of the stent. The devices and methods of the present invention are particularly useful for treating occlusive disease of the internal carotid artery. The liner may be any suitable material and suitable materials include expanded PTFE, woven dacron, nylon, low durometer silicone, or thin-walled polyethylene.

The liner is preferably mounted to a delivery catheter and is advanced over a guidewire. The liner may have an anchor at a proximal end which is used to open the proximal end of the liner. The anchor may be self-expanding or balloon expandable. Once the proximal end of the liner is opened, the liner can be designed so that blood pressure opens the liner. Alternatively, the liner may open automatically or may be opened with a separate device, the delivery catheter or the stent itself. When treating occlusive disease of the internal carotid artery, the anchor may be positioned completely in the internal carotid artery or may extend from the common carotid artery across the bifurcation of the internal and external carotid arteries and into the internal common carotid. The anchor preferably has an open structure which permits blood flow into the external carotid artery.

The liner may be an elastic liner or may be folded into a collapsed position. The liner may be collapsed in any suitable manner and preferably has a number of folded sections which are wrapped around one another. The folded sections are preferably adhered to one another to hold the liner in the collapsed position. The folded sections may be adhered together by application of heat or with an adhesive or coating. The distal end of the liner may be coated to form a curved surface which covers the ends of the folded sections. Alternatively, the ends of the liner may be scalloped or contoured so that when folded the edge tapers down more cleanly.

The liner may also be designed to evert when expanding. The everting liner reduces sliding between the liner and vessel so that plaque is not dislodged when introducing the liner. An end of the everting liner may be releasably attached to the delivery catheter.

The proximal end of the liner may also be opened with an expandable device, such as a balloon, on the delivery catheter rather than with an anchor attached to the liner. Once the proximal end is open, the stent or other device is advanced through the liner.

In yet another aspect of the invention, the catheter holds the proximal end partially open. The stent or other device is then advanced through the open proximal end. The liner can be released when using a stent or may be removed after use.

These and other features and advantages of the invention will become evident from the following description of the preferred embodiments.

The present invention is also directed to a device for lining a vessel which has an expandable anchor movable from a collapsed shape to an expanded shape. The liner attached to the anchor and extends from an end of the anchor. The liner is held between thin, flexible inner and outer layers which are preferably shrink tubing. The outer layer is retracted to expose and free the liner. The outer layer may also hold the anchor in the collapsed position.

The inner and outer layers preferably have a thickness of 0.0005–0.002 inch. The outer layer stretches over a tapered portion and is preferably flexible enough to stretch over the tapered portion as it passes over the tapered portion. The outer layer has a diameter of no more than 0.055 inch, and more preferably no more than 0.050 inch, when in the collapsed position. A radiopaque coil may also be provided which extends beyond the distal end of the liner and between the inner and outer layers. The inner layer is preferably attached to an inner element and the outer layer is preferably attached to an outer element.

BRIEF DESCRIPTION OF THE DRAWINGS

FIG. 36 shows the stent advanced through the liner.

FIG. 37 shows the stent partially expanded.

FIG. 41 shows the liner everting when deployed.

FIG. 42 shows the liner partially everted.

FIG. 45 shows another delivery catheter which holds the proximal end of the liner open.

FIG. 46 shows the stent advanced through the liner of FIG. 45.

FIG. 54C shows the liner having the anchor extending the length of the liner.

DESCRIPTION OF THE PREFERRED EMBODIMENTS

A system 2 for protecting vessels during intravascular procedures is shown in FIGS. 1–4. Although the present invention is described in relation to treatment of atherosclerotic disease of the internal carotid artery and the particular problems encountered when working in the carotid arteries, the liner may be used in other vessels such as saphenous vein grafts of coronary bypass procedures, iliac and coronary arteries. A guide catheter 4 is introduced through the femoral artery and advanced to the common carotid artery in the conventional manner. The guide catheter 4 has a hemostasis valve 6 which receives a liner delivery catheter 8. The guide catheter 4 may be omitted without departing from the scope of the invention.

Figure 1:
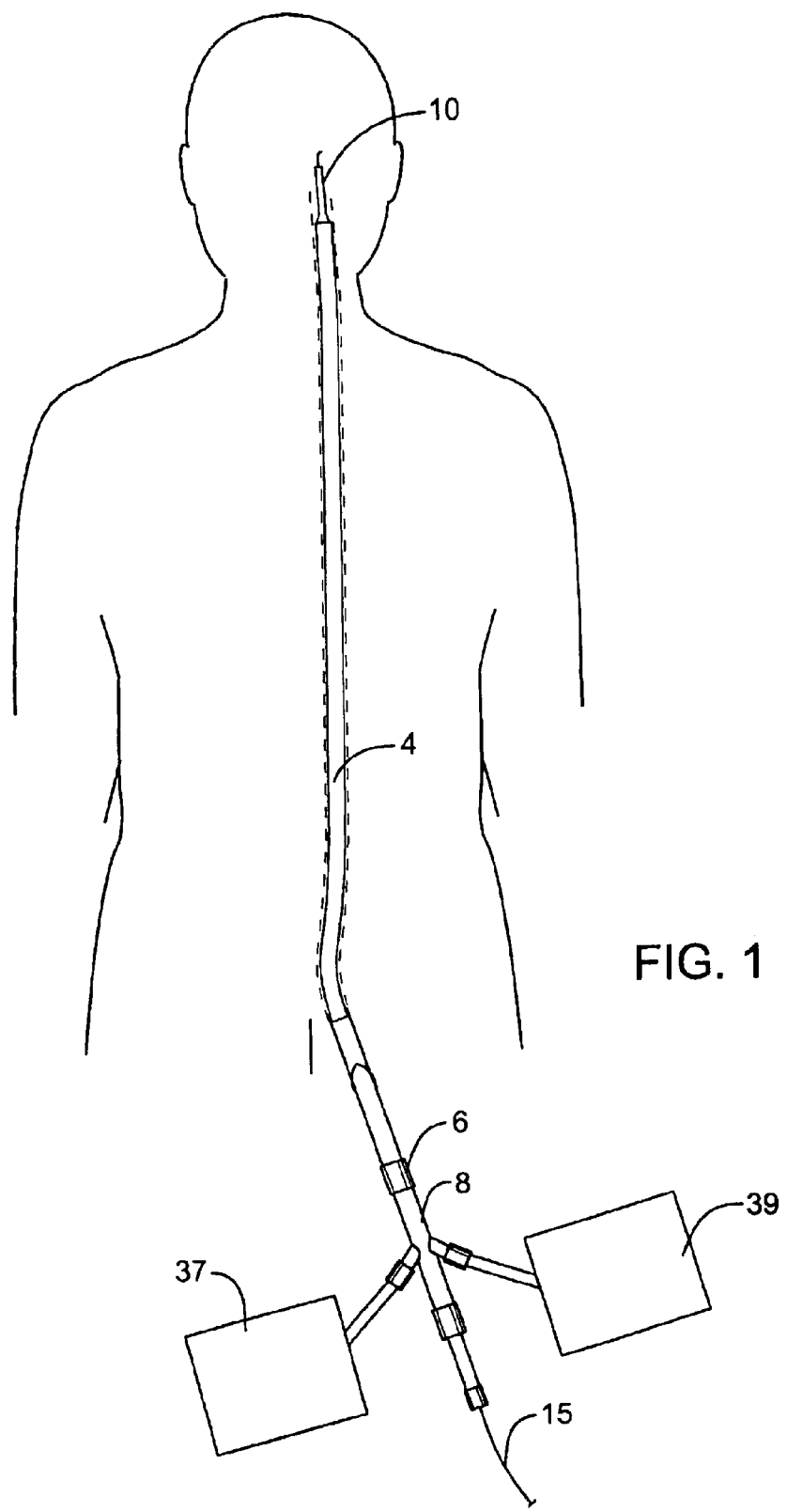
FIG. 1 shows a system for advancing devices through a narrowed region of a blood vessel such as the internal carotid artery.
Figure 2:
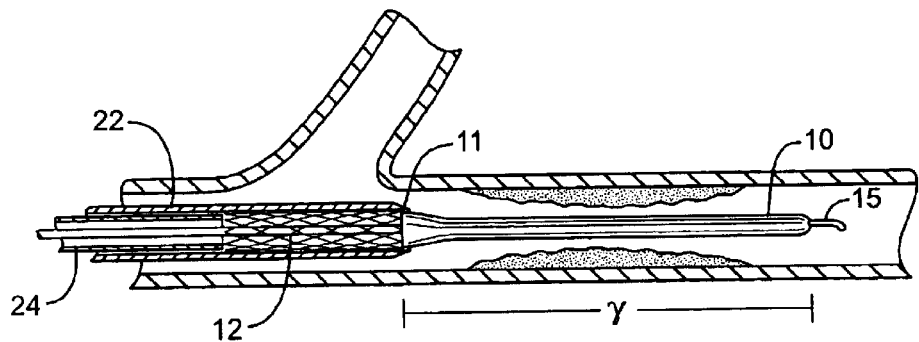
FIG. 2 shows a liner advanced through the narrowed region in a collapsed position.
Figure 3:
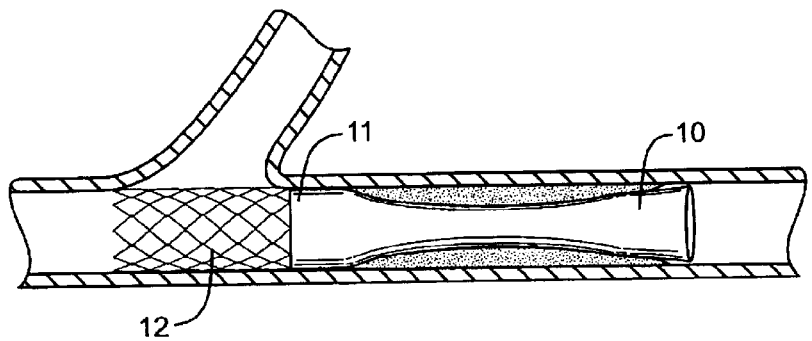
FIG. 3 shows the liner detached from the delivery catheter and expanded.
Figure 4:
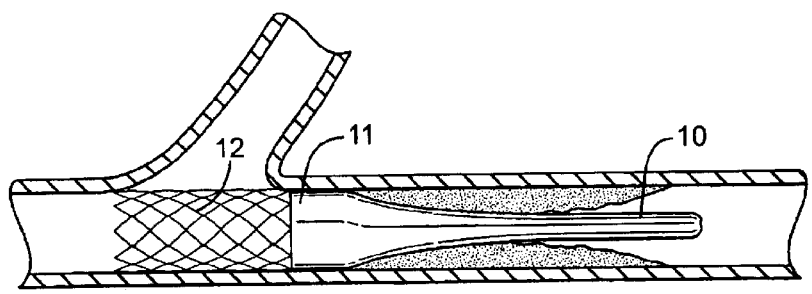
FIG. 4 shows only the proximal end of the liner expanded with an anchor.

A liner 10 is used to protect the body passageway when passing other devices through the body passageway. For example, the liner 10 may be used to protect the carotid artery to prevent plaque from being dislodged when passing other devices through the carotid artery. A proximal end 11 of the liner 10 may be attached to an anchor 12 which expands and opens the liner 10 and holds the liner 10 against the vessel wall to reduce or eliminate flow around the liner. The liner is preferably non-metallic and is relatively flexible to conform to the body passageway. The anchor 12, as will be discussed below, is mounted to one end of the liner 10 while the other end of the liner 10 is preferably free. Of course, the anchor 12 may be provided at both ends or throughout the liner 10 without departing from the scope of various aspects of the present invention. The liner 10 is advanced through the vessel in the collapsed condition of FIG. 2 so that the liner 10 can be advanced through small or highly stenosed vessels. After the liner 10 is in position, other devices, such as a stent 26 (FIG. 25) or filter (FIG. 40), may be passed through the liner 10 so that the liner 10 prevents contact between the device and the vessel wall. The liner 10 may also be used to protect the vessel when advancing other devices such as angioplasty balloons, drug delivery catheters, laser catheters or ultrasound catheters. FIG. 3 shows both ends of the liner 10 opened to trap plaque behind the liner 10 so that loose plaque cannot flow downstream. The liner 10 is preferably delivered over a conventional guidewire 15 which has a 0.010–0.018 inch diameter but may be of any other suitable size depending upon the vascular site.

Figure 6A:
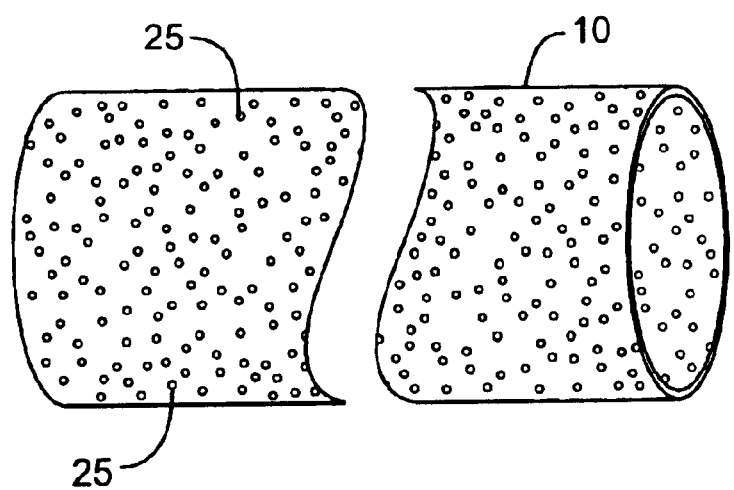
FIG. 6A shows the liner having a woven or braided configuration.
Figure 5:
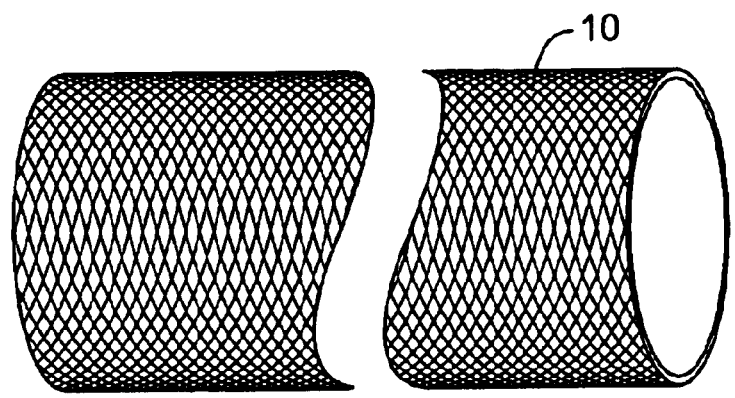
FIG. 5 shows the liner having openings or perforations.
Figure 6B:
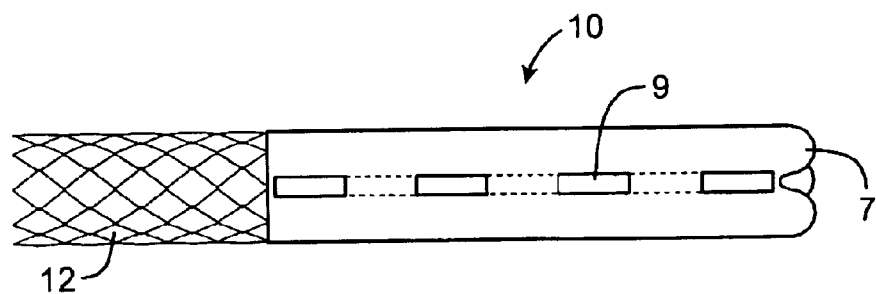
FIG. 6B shows the liner having a radiopaque maker and a scalloped distal end.

The liner 10 is preferably made of expanded PTFE having a thickness of 0.006 to 0.0005 inch, more preferably 0.001 to 0.002 inch and most preferably about 0.001+/−0.0005 inch although any other suitable material may be used. For example, the liner 10 may have a woven construction such as silk or polyester as shown in FIG. 5. The liner 10 may also have small openings 25 or perforations which act similar to a filter in that they permit blood to flow through but prevent large emboli from escaping (FIG. 6A). The openings 25 also may promote tissue growth. The liner 10 is also preferably thin enough and has a porosity sufficient to allow tissue throughgrowth. Referring to FIG. 6B, the liner 10 may also have a scalloped distal end 7 to form a smoother transition at the distal end when collapsed. The liner 10 may also have a radiopaque marker 9, such as a 0.002 inch by 0.008 inch platinum ribbon, embedded, sewn, or folded into the liner 10. The liner 10 may have the markers 9 extending longitudinally (FIG. 6B) or circumferentially. When the markers 9 extend longitudinally, three markers 9 are preferably provided 120 degrees apart.

The liner 10 may also be elastic so that the liner 10 remains substantially cylindrical and without folds in the collapsed and expanded positions. When using an elastic liner 10, the liner 10 is preferably a tube of low durometer silicone, latex or natural rubber, thermoplastic elastomers such as Kraton or hydrogenated thermoplastic isoprenes having a thickness of 0.001 to 0.0005 inch. Alternatively, the liner 10 could be made of an inelastic but plastically deformable material. Initially the liner 10 would be sized to allow easy passage of the devices such as the balloons, stents and filters described herein. The liner 10 is then plastically deformed by the devices which pass therethrough. For example, a pre-dilatation balloon may be introduced to dilate the liner 10. The stent 27 can then be advanced into the dilated liner 10 and expanded to open the narrowed vessel. Expansion of the stent continues plastic deformation of the liner 10 to a final size. Any of the liners 10 described herein may be substituted for any of the other liners 10 without departing from the scope of the invention.

Figure 7:
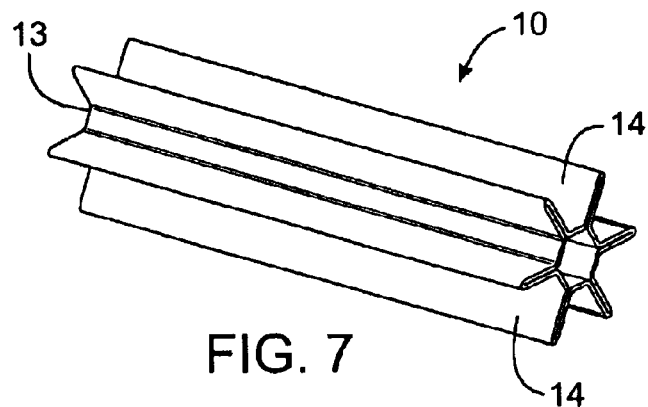
FIG. 7 shows the liner folded into six folded sections.
Figure 8:
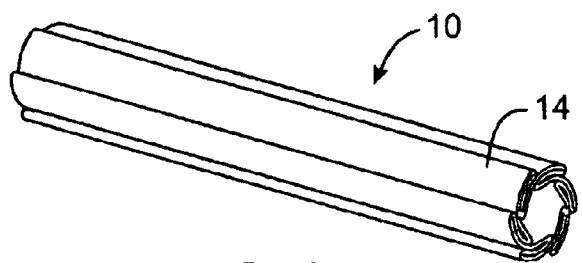
FIG. 8 shows the folded sections wrapped around one another.
Figure 9:
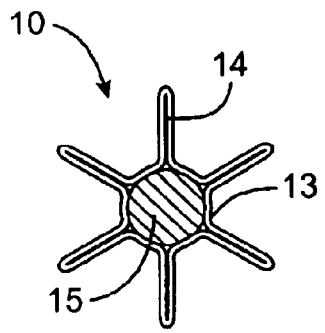
FIG. 9 shows an end view of the liner of FIG. 7.
Figure 11:
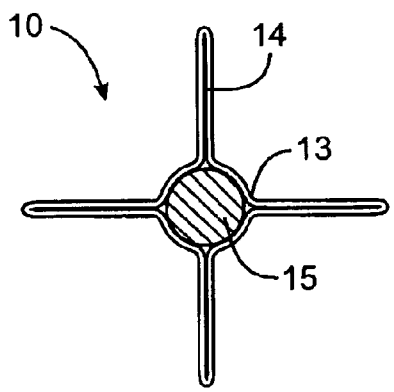
FIG. 11 shows the liner having four folded sections.
Figure 10:
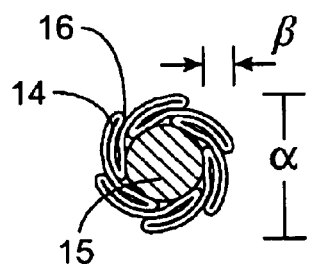
FIG. 10 shows an end view of the liner of FIG. 8 with the liner wrapped around a guidewire.
Figure 12:
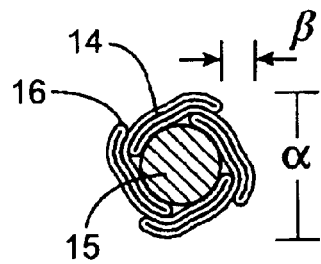
FIG. 12 shows the liner of FIG. 11 with the folds wrapped around one another.
Figure 13:
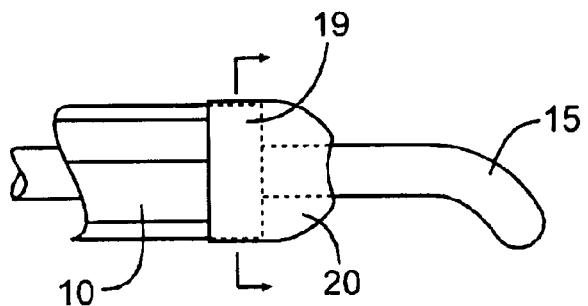
FIG. 13 shows a coating over a distal end of the liner.
Figure 14:
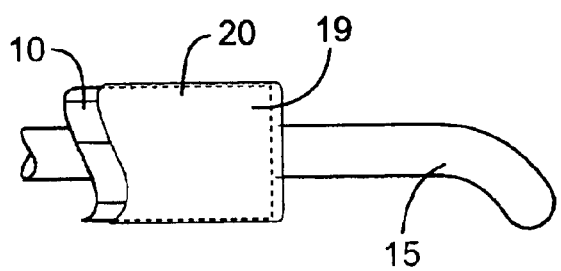
FIG. 14 shows the coating extending over the length of the liner.
Figure 15:
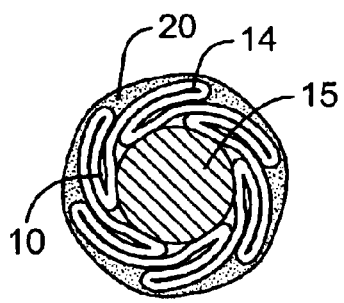
FIG. 15 is a cross-sectional view of the liner and coating with four folded sections.
Figure 16:
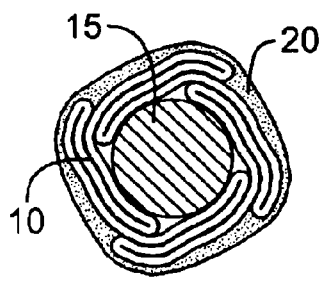
FIG. 16 is a cross-sectional view of the liner and coating with six folded sections.

FIGS. 7–12 show a preferred method of collapsing the liner 10. The liner 10 is folded longitudinally along creases 13 to create at least 2 and preferably 4–6 folded sections 14. Four folded sections 14 are shown in FIG. 11 and six folded sections 14 are shown in FIG. 7 and 9. The folds 14 are then wrapped as shown in FIGS. 8, 10 and 12. The liner 10 may, of course, be wrapped in any other manner. For example, the liner 10 may be spiral wrapped or randomly compressed and set with high pressure and/or heat. The folded sections 14 may be adhered to one another by application of heat which holds the folded sections 14 together without melting and fusing the sections 14 together. Another method of holding the liner 10 in the collapsed position is to apply an adhesive 16 such as medical grade glue, cyanoacrylates, epoxies, ultraviolet activated adhesives, low molecular weight polyvinyl alcohol polymer, gelatin and sucrose. The liner 10 may also be partially or completely covered with a coating 20 which dissolves in blood such as sugar (FIGS. 13–16). In particular, the distal end 19 of the liner 10 may be covered with the coating 20 to form a smooth, atraumatic end as shown in FIG. 13. The coating 20 may extend along the length of the liner 10 as shown in FIG. 14 or may be only at the distal end or intermittent as shown in FIG. 13.

Figure 17:
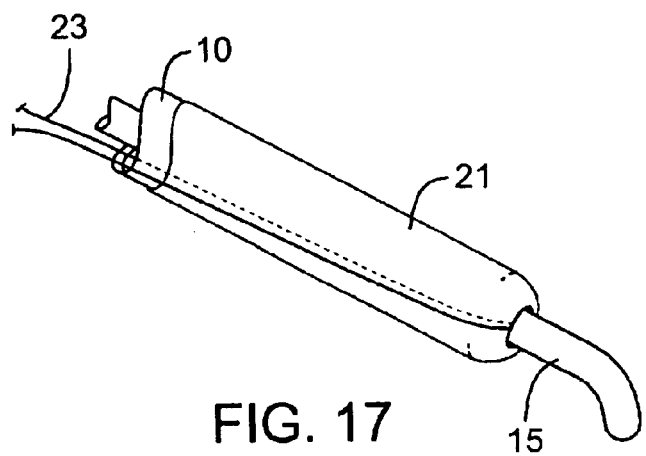
FIG. 17 shows a sheath covering the liner in the collapsed condition.
Figure 18:
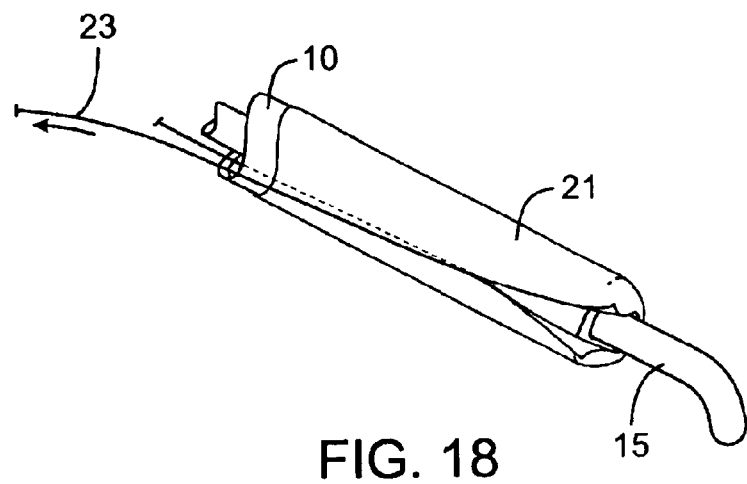
FIG. 18 shows a filament tearing a distal end of the sheath.

The liner 10 may also be covered by a removable sheath 21 as shown in FIGS. 17 and 18. The sheath may be removed in any manner such as tearing along perforations or with a chemical, thermal or electrolytically severable bond. A filament 23 may also be used to tear the sheath 21 as shown in FIGS. 17 and 18. The filament 23 may have both ends extending through the catheter rather than having one end extend out of the catheter. The filament 23 is shown separated from the sheath 21 for clarity but would either pass inside the sheath 21 or would be partially embedded in the sheath 21. The sheath 21 can also be a simple retractable sheath 21 as is known in the art.

Referring again to FIGS. 10 and 12, the liner 10 is collapsed onto the guidewire 15 so that the liner 10 has an outer diameter α of no more than 0.065 inch, more preferably no more than 0.040 inch, and most preferably no more than 0.026 inch. Stated another way, the thickness β of the liner 10 is preferably no more than 0.015 inch, more preferably no more than 0.012 inch, and most preferably no more than 0.008 inch when measured in a radial direction. For a guidewire 15 having a 0.014 inch diameter, the liner 10 is preferably collapsed so that the outer diameter α is 0.020 to 0.032 inch, preferably about 0.026 inch, and the thickness β of the liner 10 is 0.004 to 0.008 inch, preferably about 0.006 inch. For a guidewire 15 having a 0.018 inch diameter, the liner 10 is preferably collapsed so that the outer diameter α is still about 0.020 to 0.032 inch, preferably about 0.026 inch, and the thickness β of the liner 10 is 0.003 to 0.006 inch, preferably about 0.004 inch. The liner 10 also has a high ratio of collapsed cross-sectional area to expanded circumference in the range of 1:10 to 1:30 and preferably at least 1:20.

The relatively small size of the liner 10 advantageously permits the liner 10 to be introduced through small and heavily stenosed vessels. The carotid artery is often occluded 95 to 98% and may have diameters as small as 0.020 inch or even 0.010 inch before surgical or interventional procedures are performed. Conventional stents used in the internal carotid artery have a collapsed diameter of about 0.065 to 0.092 inch and, thus, must often displace the plaque to pass through the vessel. It is believed that some strokes which occur when using stents in the carotid artery are caused by plaque which is dislodged when the stent is advanced through and expanded within highly stenosed regions. The liner 10 of the present invention protects the vessel as the stent or other device is passed through the vessel. The liner 10 preferably has a length γ of at least 2 cm and preferably 2–10 cm (FIG. 2). The liner 10 and anchor 12 have a diameter of 4–10 mm in the expanded condition with the specific size selected depending upon the size of the vessel being treated. The relative dimensions shown in the drawing have been exaggerated to illustrate the features of the invention. In fact, the liner 10 has a length to width ratio (γ to α) in the collapsed position of at least 20 to 1, 50 to 1, 80 to 1, and even up to 200 to 1 depending upon the particular application. The liner 10 preferably increases in outer diameter at least 5, more preferably at least 6 and most preferably at least 8 times when moving from the collapsed to expanded positions.

Referring again to FIGS. 3 and 4, the anchor 12 may be attached to the proximal end 11 of the liner 10 to expand the end 11 of the liner 10, hold the liner 10 in position and reduce flow around the liner 10. The anchor 12 may be any suitable device including a commercially available nitinol or stainless steel stent such as the MULTILINK manufactured by ACS and the NIR manufactured by Scimed. The liner 10 is attached to a portion of the anchor 12 with an adhesive, mechanical interconnection, thermal bond, suture or the like, or fused or soldered with radiopaque wire or ribbon. The liner 10 may, of course, be attached in any other manner. The liner 10 may also be encapsulated between layers of expanded PTFE.

Figure 19:
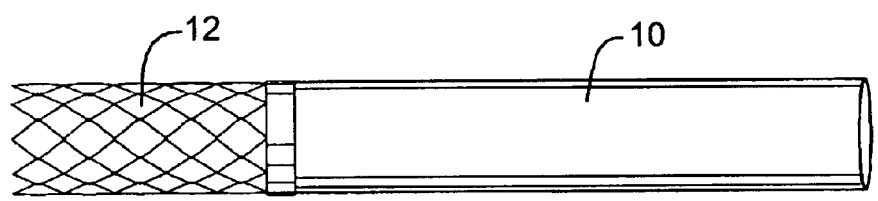
FIG. 19 shows the liner attached to the anchor.
Figure 20:
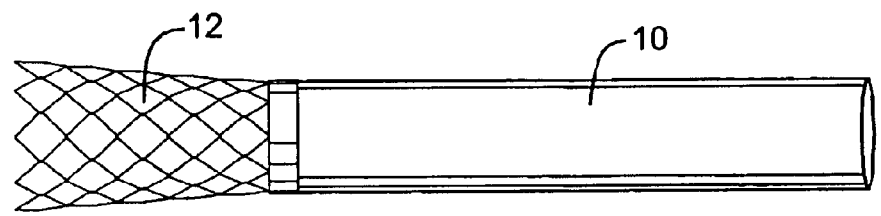
FIG. 20 shows the liner attached to a tapered anchor.

The anchor 12 and liner 10 may form a continuous, cylindrical shape in the expanded position (FIG. 19) or the anchor 12 may have a tapered shape, (FIG. 20). The tapered shape of the anchor 12 may be useful when used in the carotid arteries with the small end positioned in the internal carotid artery and the large end in the common carotid. A method of forming the expanded shape of FIG. 20 is for the anchor 12 to have a larger diameter than the liner 10 so that the liner 10 holds an end of the anchor 12 at a smaller diameter. For example, the anchor 12 may be a stent having an 8 mm diameter with the liner 10 having a 6 mm expanded diameter so that the liner 10 holds the end 11 of the anchor 12 to about 6 mm. Alternatively, the anchor 12 could be designed to expand to different predetermined diameters at different points along its length by varying strut lengths along its length.

The anchor 12 is positioned within an anchor retention catheter 22 (FIG. 2). The anchor 12 is naturally biased to the expanded condition of FIG. 3 and is held in the collapsed position by the retention catheter 22. The anchor 12 is deployed by retracting the catheter 22 while an inner element 24 holds the anchor 12 at the desired location in the vessel. The liner 10 is advanced over the guidewire 15 which is advanced ahead of the catheter 22.

Figure 21:
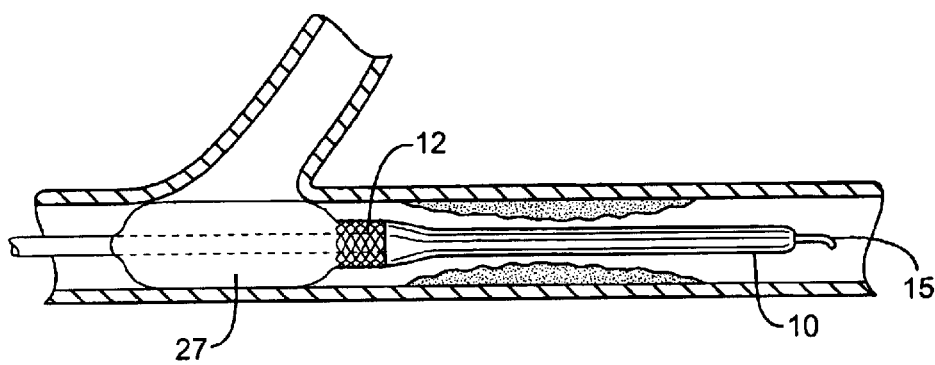
FIG. 21 shows an anchor contained entirely within the internal carotid artery.
Figure 22:
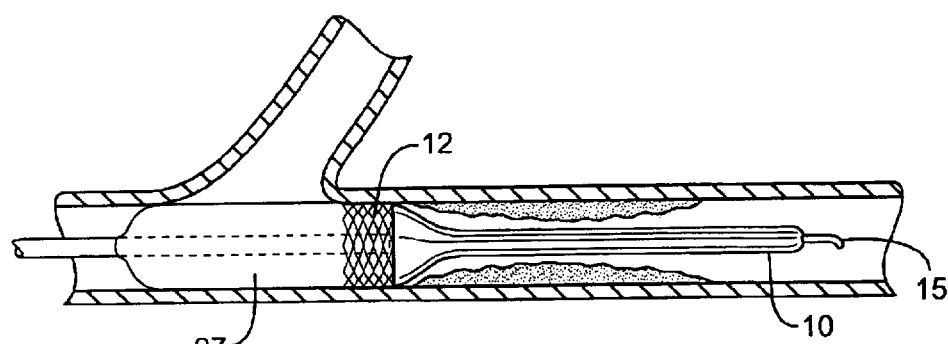
FIG. 22 shows the balloon expanding the anchor and blocking blood flow into the internal carotid artery.
Figure 23:
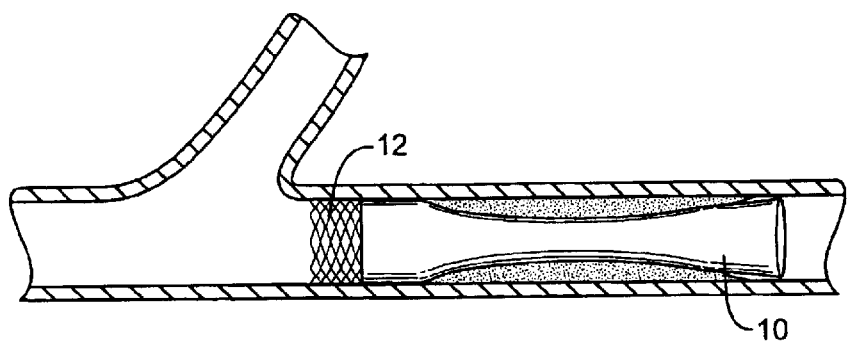
FIG. 23 shows the liner and anchor of FIG. 22 deployed.
Figure 24:
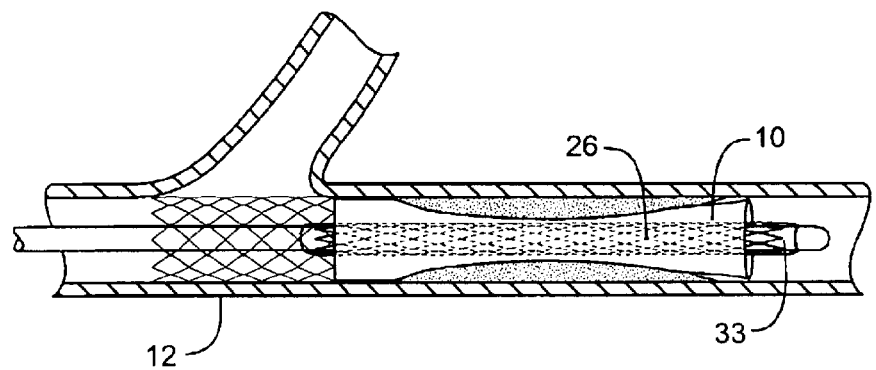
FIG. 24 shows a balloon-expandable stent introduced into the liner.

The anchor 12 may be deployed to extend into the common carotid artery at the bifurcation of the external and internal carotid arteries (FIG. 2) or may be contained entirely within the internal carotid artery (FIGS. 21–23). The anchor 12 may also be deployed by inflating a balloon 27 as shown in FIG. 21 or may be a shape memory material which is heat activated. When using a balloon 27 to expand the anchor 12, the anchor 12 is preferably a conventional nitinol or stainless steel stent although any suitable stent or device may be used. The balloon 27 is preferably compliant so that a proximal portion of the balloon 27 expands to occlude the vessel as shown in FIG. 21 before expansion of the anchor 12. Alternatively, the balloon could be non-compliant but designed to inflate at a lower pressure than that required to expand the stent. By occluding the vessel, blood flow through the vessel is stopped so that even if plaque is released the plaque will not flow downstream. Further inflation of the balloon 27 (using inflation source 39) expands the anchor 12 into engagement with the vessel wall (FIG. 22). Any of the embodiments of the liner 10 described herein may be used with balloon or self-expanding anchors 12 and stents 26.

Figure 26A:
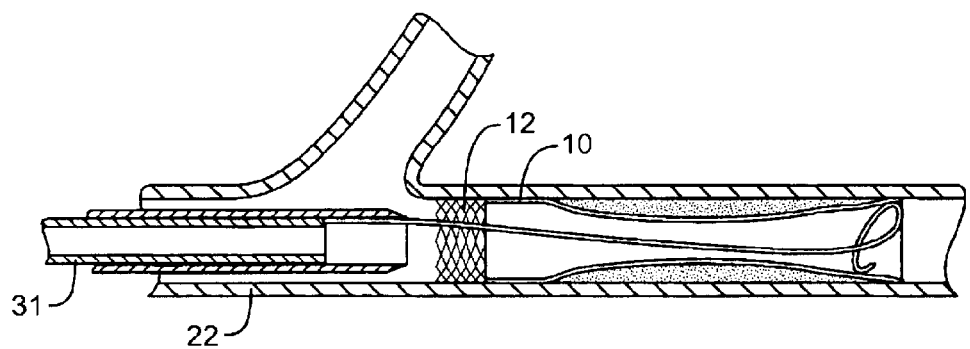
FIG. 26A shows an elongate element which opens the distal end of the liner.

After the anchor 12 has been expanded, the liner 10 can be configured to automatically open with blood pressure (FIG. 3). Alternatively, the catheter 22 may be advanced through the liner 10 to partially open the liner 10. The device, such as the stent 26, may also be advanced through the liner 10 to open the liner 10. The liner 10 protects the vessel to prevent intravascular devices from dislodging plaque when passing through the vessel. The distal end of the liner 10 may also be opened with an elongate element 29, such as a nitinol wire, advanced into the liner 10 to open the liner 10 as shown in FIG. 26A. The element 29 may be advanced and retracted independently with an inner actuator 31.

Figure 26B:
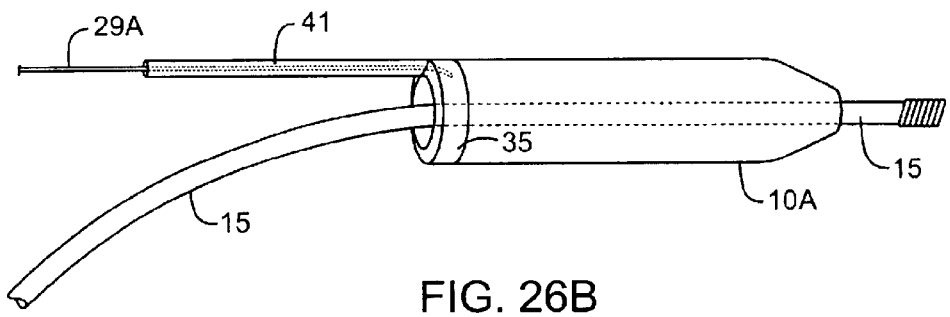
FIG. 26B shows the elongate element contained within a tube during delivery the liner.
Figure 26C:
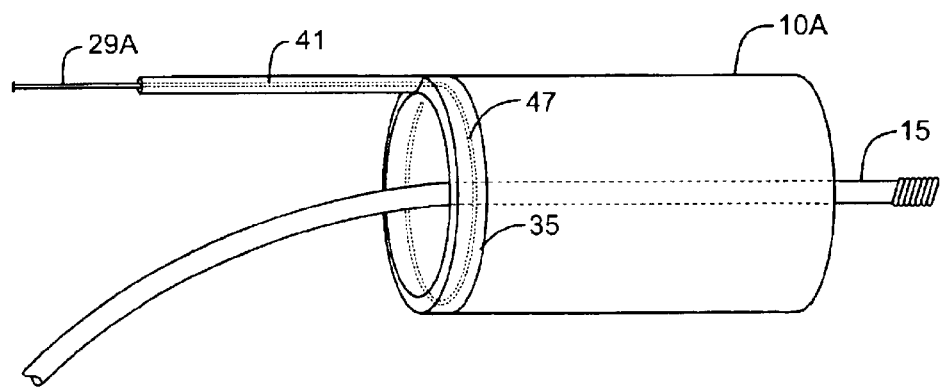
FIG. 26C shows the elongate element of FIG. 26B advanced into a pocket of the liner to open the proximal end of the liner.

Referring to FIGS. 26B and 26C, the elongate element 29A may also be advanced into a pocket 35 in liner 10A. The pocket 35 is preferably formed by simply inverting or everting the end of the liner 10A and attaching the end to another part of the liner 10A to form the pocket 35. The elongate element 29A passes through a tube 41, preferably a hypotube, polymer tube or composite tube, which is releasably attached to the pocket 35. The tube 41 is preferably released by heat, electrolytic detachment, mechanical detachment, dissolution of a bond by blood, or retraction of a retention cord although any suitable method may be used.

Figure 26D:
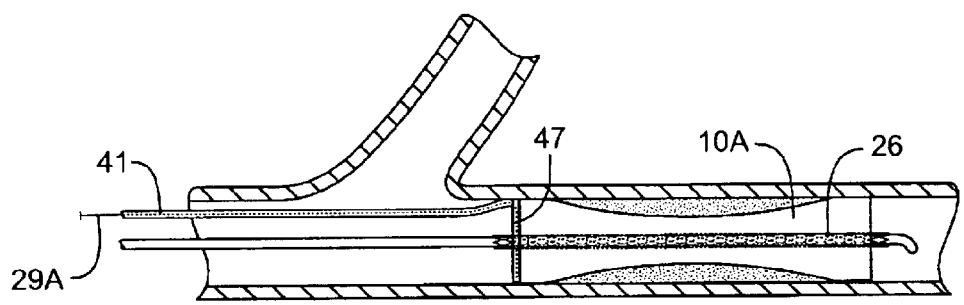
FIG. 26D shows the stent introduced into the liner of FIG. 26C.
Figure 26E:
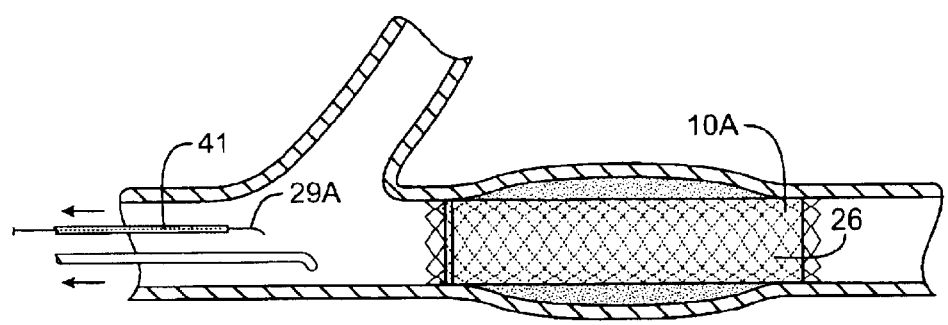

The elongate element 29A is preferably made of a superelastic material, such as nitinol, which forms a loop 47 in the expanded position. The elongate element 29A is contained within the tube 41 when the liner 10A is advanced through the vasculature. The liner 10A is advanced over the guidewire 15 by pushing the tube 41. When the user is ready to expand the proximal end of the liner 10A, the element 29A is advanced into the pocket 35 so that the loop 47 opens the liner 10A as shown in FIGS. 26C and 26D. After opening the proximal end of the liner 10A, the liner 10 may be used in any manner described herein. For example, the stent 26 may be advanced into the liner 10A to open the narrowed region of the blood vessel as described in further detail below and shown in FIGS. 26D and 26E.

Figure 25:
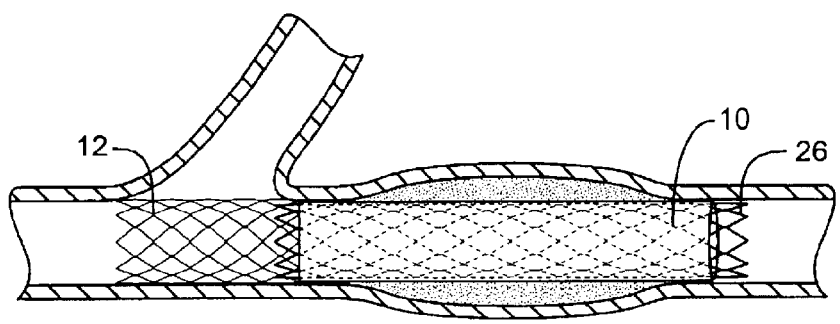
FIG. 25 shows the stent expanded.
Figure 27:
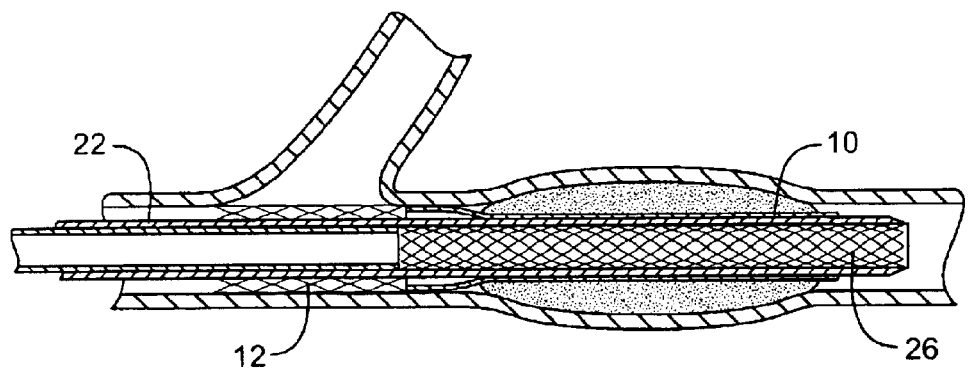
FIG. 27 shows the delivery catheter for the anchor used to deliver a stent into the liner.
Figure 28:
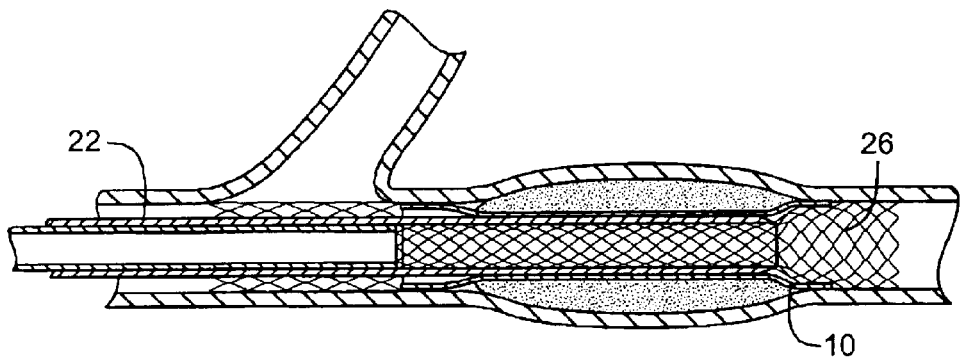
FIG. 28 shows the distal end of the stent of FIG. 27 expanded to trap plaque behind the liner.
Figure 29:
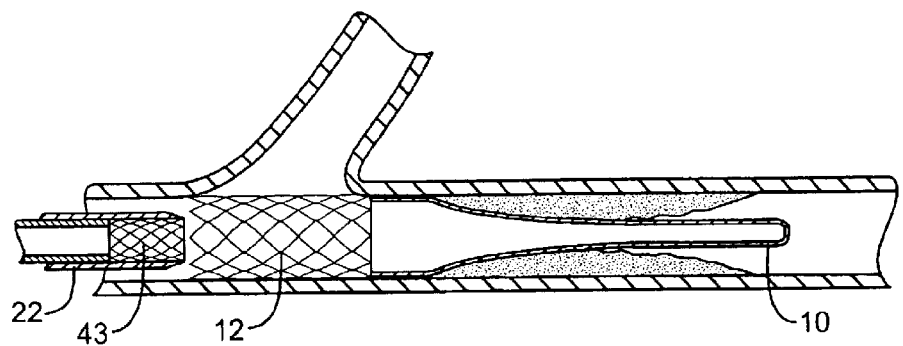
FIG. 29 shows the delivery catheter for the anchor used to deliver a distal anchor.
Figure 30:
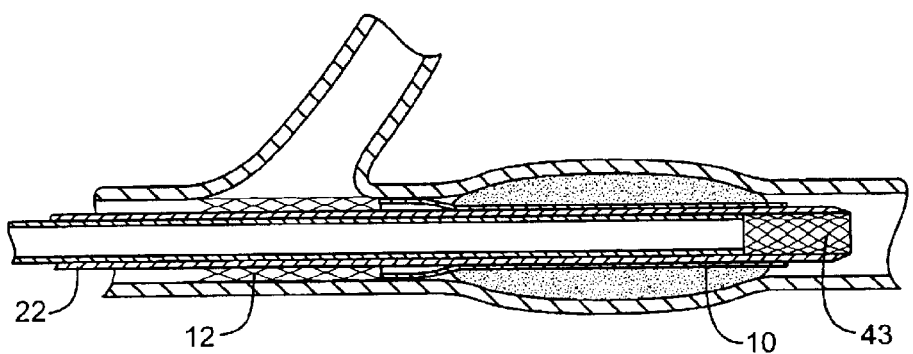
FIG. 30 show the delivery catheter in position for delivering the distal anchor.
Figure 31:
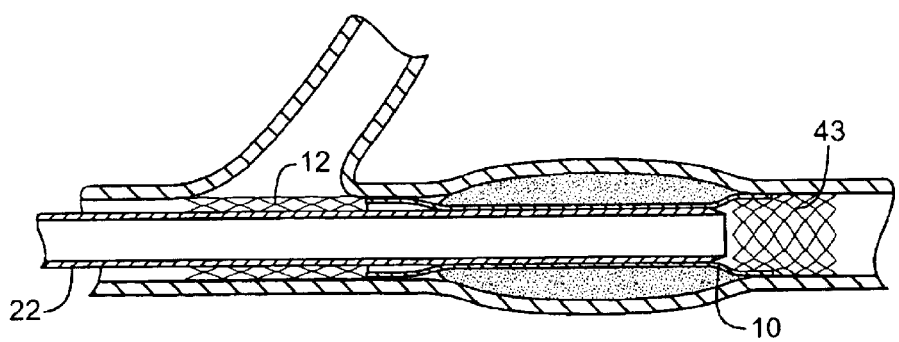
FIG. 31 shows the distal anchor deployed so that the proximal and distal ends of the liner are expanded.
Figure 32:
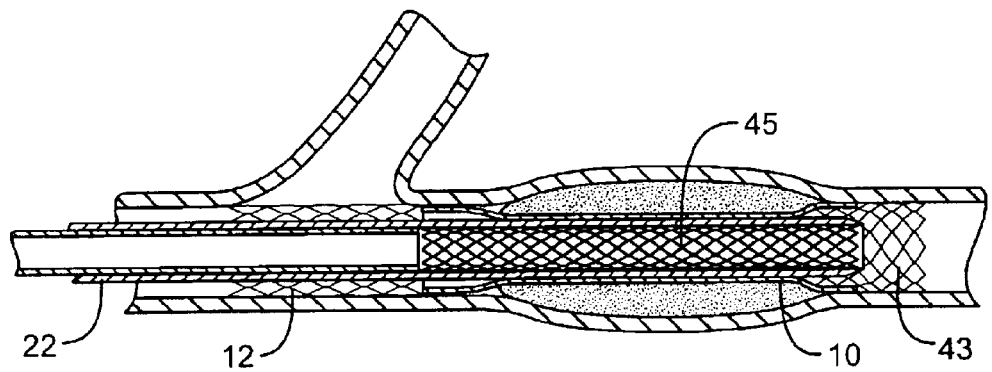
FIG. 32 shows another stent delivered between the proximal and distal anchors.
Figure 33:
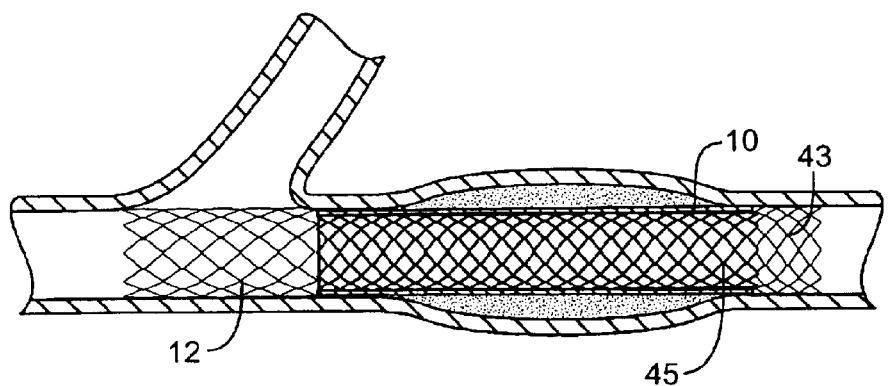
FIG. 33 shows the stent of FIG. 32 expanded.
Figure 34:
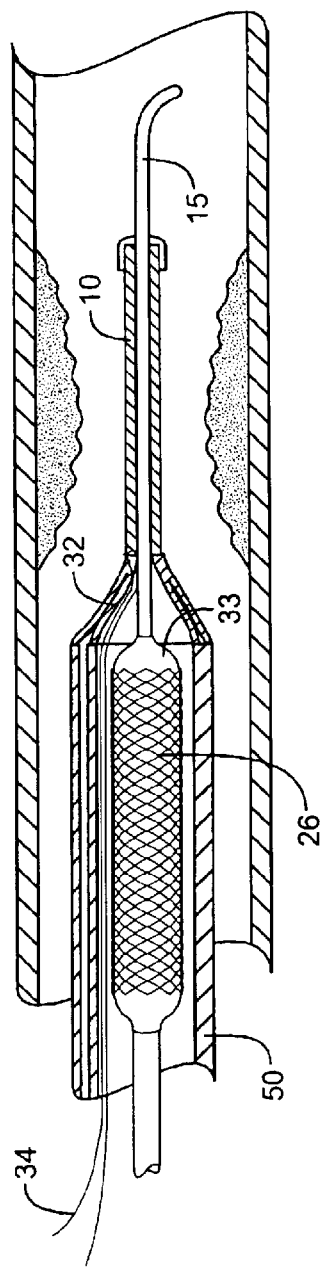
FIG. 34 shows a delivery catheter having an expandable section for opening the proximal end of the liner.

When the device introduced into the liner 10 is the stent 26, the stent 26 is preferably expanded to open the narrowed portion of the vessel as shown in FIG. 25. The stent 26 is mounted to a balloon 33 which is coupled to an inflation source 37 (FIG. 1) for inflating the balloon 33. The stent 26 is preferably a conventional nitinol or stainless steel stent. The delivery catheter 22 is preferably introduced into the liner 10 as shown in FIG. 27 with the distal end of the catheter 22 positioned beyond the end of the liner 10. The catheter 22 is then retracted to expose the distal end of the stent 26. The distal end of the stent 26 is preferably opened first so that plaque is trapped between the anchor 12 and stent 26 when expanding the rest of the stent 26. The liner 10 may have the openings 25 (FIG. 5) which effectively filter blood trapped behind the liner 10 and help to equalize pressure on opposite sides of the liner as the stent 26 is expanded. The catheter 22 may also be used to deliver a distal anchor 43 which holds the distal end of the liner 10 open as shown in FIGS. 29–31. Of course, the distal anchor 43 may be already attached to the liner 10 before introduction without departing from the scope of the invention. Another stent 45 can then be delivered to expand the liner 10 between the anchor and distal anchor 43 (FIGS. 32 and 33).

Referring to FIGS. 34–39, the proximal end of the liner 10 may be expanded by delivery catheter 50 and then released so that the anchor 12 is not required. The catheter 50 has an expanding section 32 which is preferably inflatable but may also be mechanically actuated. The expanding section 32 is coupled to a lumen for inflating Ad the expanding section 32. The liner 10 is attached to the expanding section 32 with any suitable connection such as glue, suture, or soldered with radiopaque wire or ribbon. The liner 10 is preferably attached to the expanding section 32 with a thread 34 which passes through the liner 10 and expanding section 32. An end of the thread 34 is pulled to release the liner 10.

Figure 35:
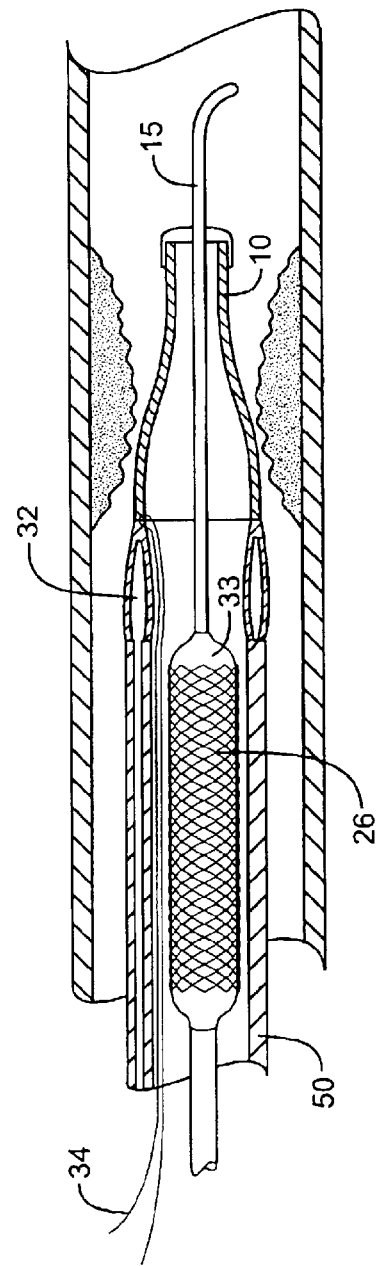
FIG. 35 shows the proximal end of the liner opened with the expandable section.
Figure 38:
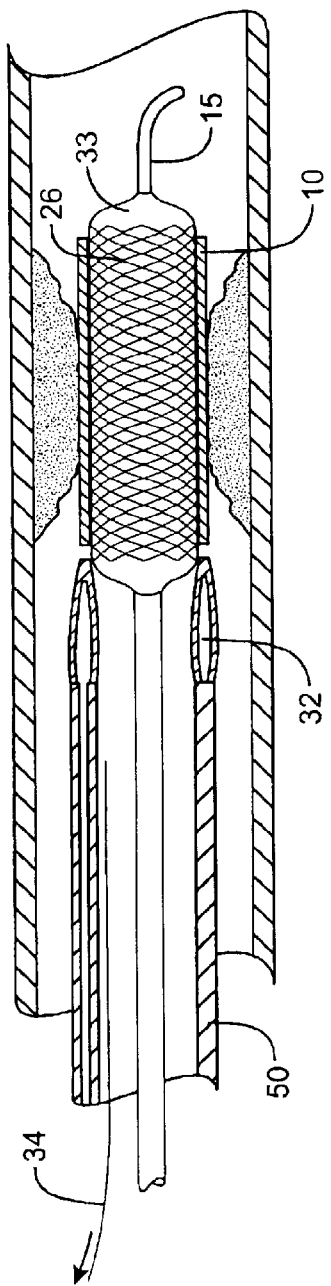
FIG. 38 shows the stent expanded into contact with the vessel wall and the liner released from the delivery catheter.
Figure 39:
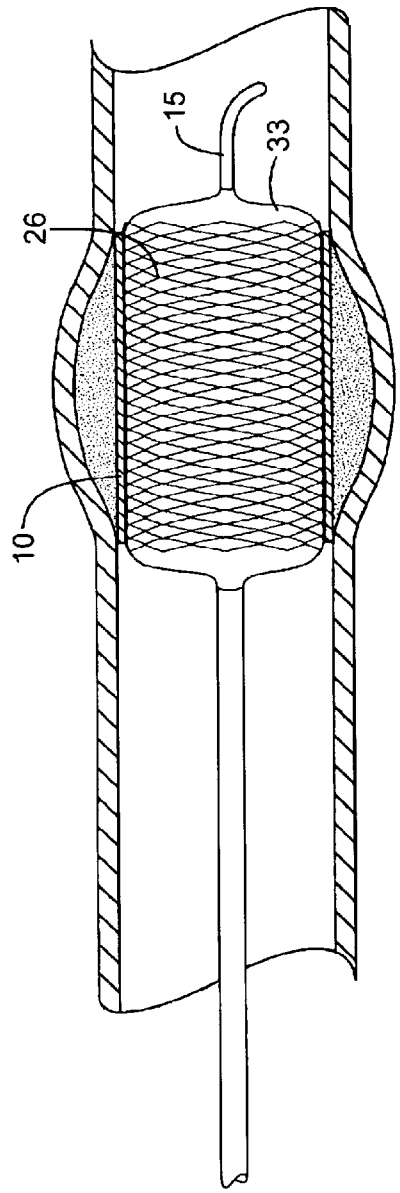
FIG. 39 shows the stent fully expanded.
Figure 40:
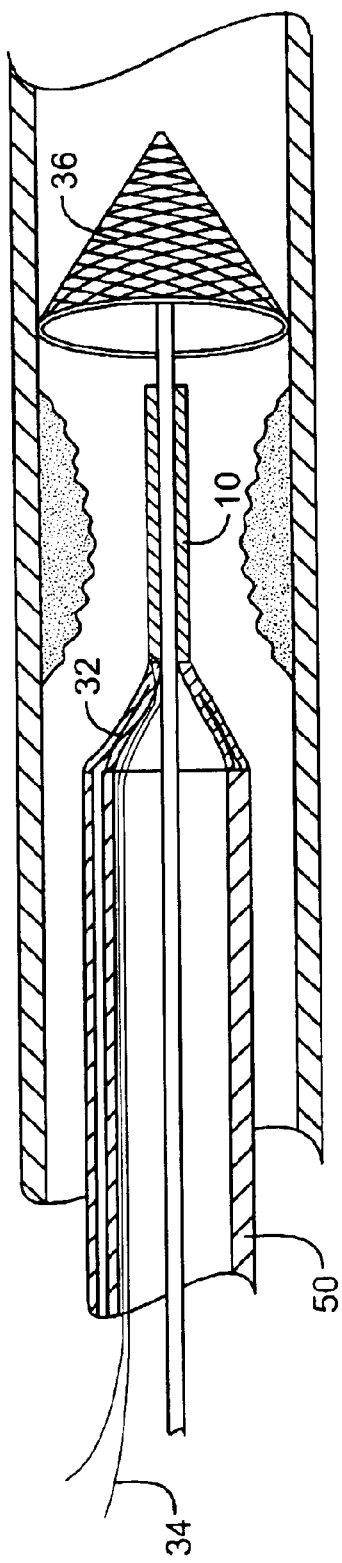
FIG. 40 show a filter passed through the liner.

The expanding section 32 is inflated to expand the proximal end of the liner 10 as shown in FIG. 35. The stent 26 or other device may then be passed through the liner 10 to open the liner 10 further as shown in FIG. 35. Referring to FIG. 38, the stent 26 is partially expanded so that the liner 10 is held firmly in place by the stent. The liner 10 is then detached by pulling the thread 34 and the stent 26 is fully expanded. Referring to FIG. 40, the device may also be a filter 36 which is advanced through the liner 10 to trap dislodged plaque during an angioplasty, stent or other procedure. The liner 10 may then be removed before removing the filter 36 or may be used to line the vessel when deploying the stent 26.

Figure 43:
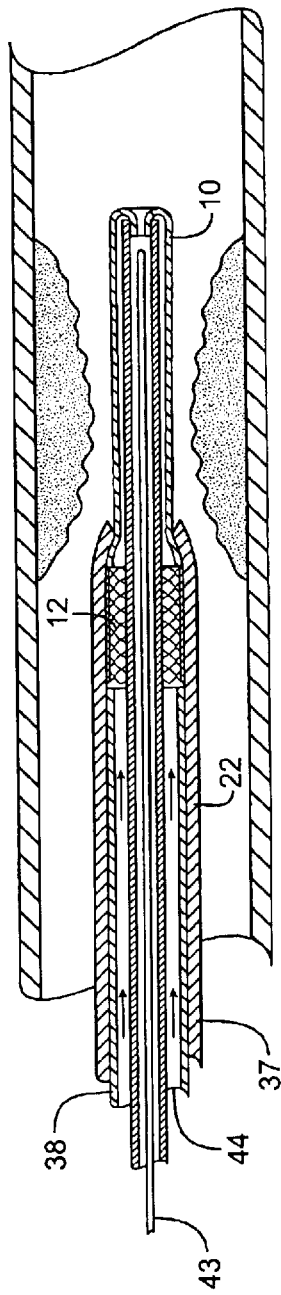
FIG. 43 shows the liner almost completely everted and the distal end released.
Figure 44:
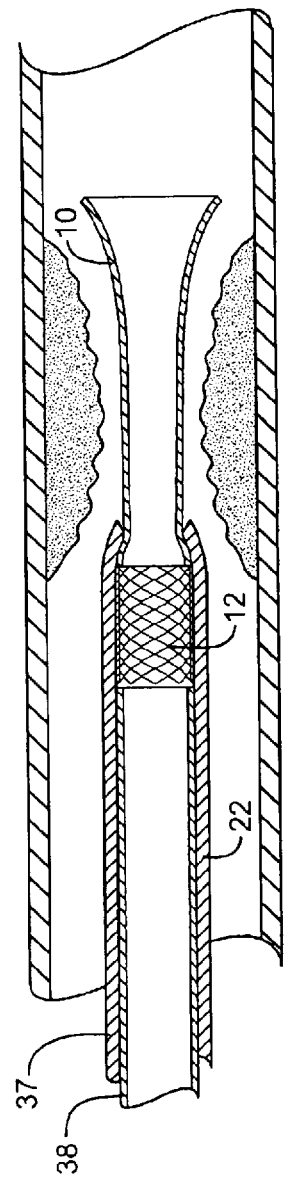
FIG. 44 shows the liner released from the delivery catheter.

Referring to FIGS. 41–44, the liner 10 may also be everted when moving from the collapsed to expanded positions. The liner 10 has the anchor 12 which is self-expanding and held in the collapsed position by retention catheter 37. Pusher element 38 holds the anchor 12 in place while retracting the retention catheter 37. A proximal end 40 of the liner 10 is releasably attached to an inner member 42. The liner 10 is pressurized, preferably with saline, using lumen 44 in the pusher element 38. Once the liner 10 is pressurized, the inner member 42 is advanced so that the liner 10 everts and moves through the vessel as shown in FIGS. 42–43. An advantage of the everting liner 10 is that sliding forces between the liner 10 and the vessel wall are reduced when advancing the liner 10.

After the liner 10 has been fully everted, the retention catheter 37 is retracted so that the anchor 12 expands and holds the proximal end of the liner 10 open. The liner 10 is then detached from the inner member 42. The liner 10 may have a mechanical connection which is released with a push rod or guidewire 43. The liner 10 may also have a severable bond with the inner member 42 such as a thermally, chemically or electrolytically severable bond using the guidewire 43. The device, such as the stent 26, is then delivered through the liner 10.

Referring now to FIGS. 45 and 46, the liner 10 may also be held open slightly at the proximal end 11 by delivery catheter 60. The proximal end 11 of the liner is preferably held open to a diameter of 6 mm to 8 mm or 4 Fr to 7 Fr. One or more filaments 62 hold the liner to the catheter 60. The liner 10 extends over the distal end of the catheter 60 but may also be mounted inside the catheter 60. The filaments are shown separated from the body of the catheter 60 for clarity but would, of course, either pass through the catheter or be held close to the catheter 60. The distal end of the stent 26 is inflated first to trap the plaque behind the liner 10 and reduce flow around the liner 10. The rest of the stent 26 is then expanded in the conventional manner.

Figure 47:
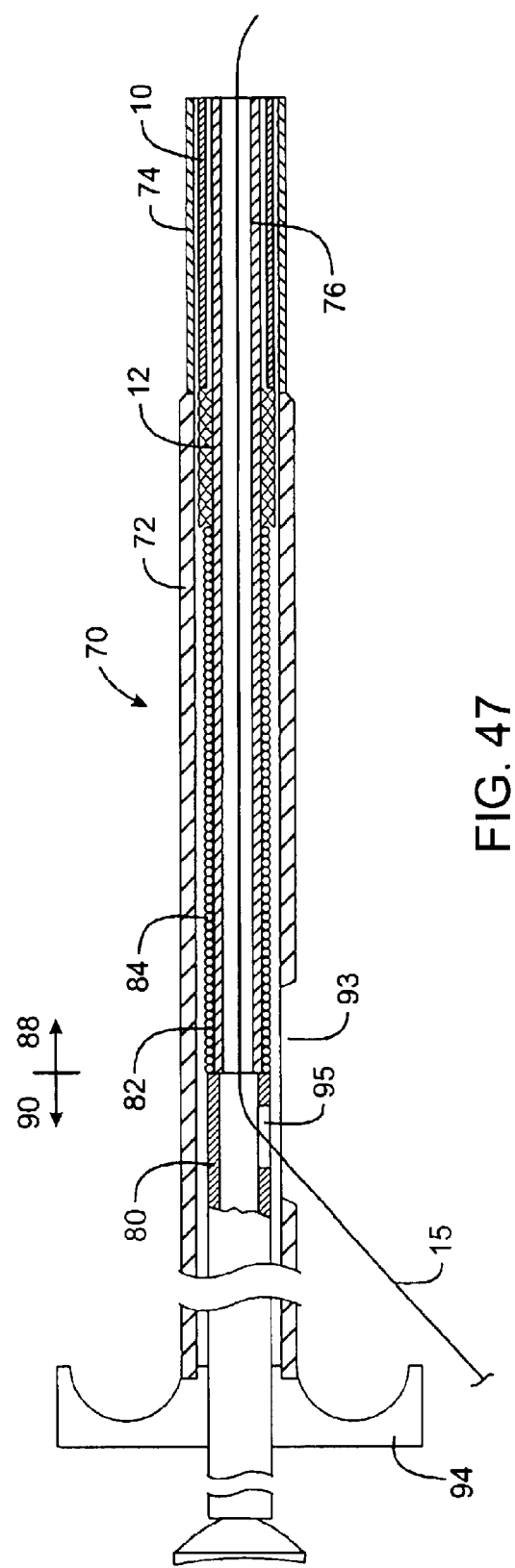
FIG. 47 shows another delivery catheter for the liner.

Referring to FIG. 47, another catheter 70 for delivering the liner 10 is shown wherein the same or similar reference numbers refer to the same or similar structure. The catheter 70 operates similar to catheter 22 described above in that the liner 10 is mounted to the self-expanding anchor 12. The anchor 12 is held in the collapsed position of FIG. 47 by an outer wall 72 of the catheter 70. The outer wall 72 is retracted to expose the anchor 12 and permit the anchor 12 to expand.

The liner 10 is positioned between a flexible sheath 74 and an inner tube 76. The sheath 74 and inner tube 76 prevent the liner 10 from contacting the walls of the vessel and guidewire 15 when the liner 10 is advanced through the vasculature. The sheath 74 and tube 76 also hold the liner 10 in the collapsed position although the liner 10 may be collapsed without requiring the sheath 74 and tube 76. The sheath 74 is attached to the outer wall 72 and is retracted together with the outer wall 72.

Figure 48:
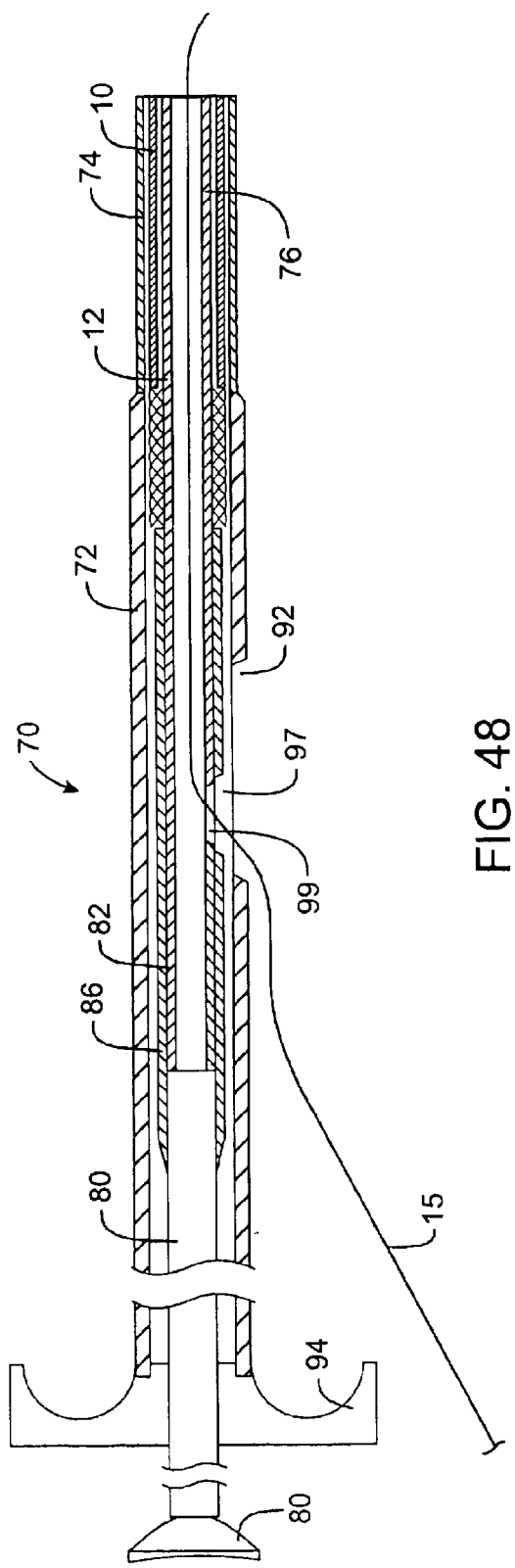
FIG. 48 shows still another delivery catheter for the liner.

A shaft 80 extends through the catheter 70 and a flexible shaft extension 82 extends from the shaft 80. The shaft extension 82 and inner tube 76 provide a relatively flexible distal portion to navigate tortuous vessels such as the cerebral vasculature. The flexible shaft extension 82 may be a coil 84 as shown in FIG. 47 or may be a tube 86 of material as shown in FIG. 48. A distal portion 88 of the catheter 70, which extends from the distal end of the shaft 80, is preferably more flexible than a proximal portion 90 which terminates at the end of the shaft 80.

Referring to FIG. 47, the guidewire 15 passes through slots 93, 95 in the outer wall 72 and shaft 80 for loading the device on the guidewire 15. Referring to FIG. 48, the guidewire 15 may also pass through slots 92, 97, 99 in the outer wall 72, inner tube 76 and shaft extension 82. The catheter 70 may, of course, have a continuous lumen which extends to the proximal end of the catheter 70. Referring again to FIG. 47, a handle 94 is attached to the outer wall 72 and is pulled relative to the shaft 80 to retract the sheath 74 and outer wall 72. The outer wall 72 is preferably made of high density polyethylene having a thickness of about 0.005 inch and an outer diameter of 0.040 to 0.070 inch, preferably about 0.055 inch. The outer wall 72 preferably has a length of 110 to 150 cm and preferably about 135 cm. The sheath 74 is preferably made of linear low density polyethylene having a wall thickness of about 0.002 inch and an outer diameter of about 0.049 inch. The inner tube 76 is preferably made of polyimide having a wall thickness of 0.0005 to 0.001 inch and an outer diameter of 0.014 to 0.026 inch, more preferably 0.018 to 0.024 inch and most preferably about 0.022 inch. The liner 10 is collapsed to have a diameter, length, thickness and length to thickness ratios as described above when mounted to the tube 76. The shaft 80 is preferably a 0.022 inch diameter stainless steel mandrel and the shaft extension 82 is preferably a stainless steel coil. The shaft extension is fused to the inner tube 76 (FIG. 47). The extension 82 may also be a tube of linear low density polyethylene which is extruded and then irradiated with 25/30 Mrads to an outer diameter of about 0.040 and a wall thickness of about 0.018 inch (FIG. 48). Any other suitable materials may be used without departing from the scope of the invention.

The catheter 70 and liner 10 are used in substantially the same manner as the catheters and liners 10 described above and the discussion above is equally applicable here. The liner 10 is advanced over the guidewire 15 to a narrowed region of a blood In vessel such as the internal carotid artery. The liner 10 and catheter have a small profile, as discussed above and incorporated here, so that the liner 10 may be advanced into the narrowed region without dislodging plaque. When the liner 10 is at the desired location, the handle 94 and shaft 80 are manipulated to retract the sheath 74 and the outer wall 72. When the outer wall 72 and sheath 74 are retracted, the anchor 12 is free to expand. The liner 10 may then be used in the manner described above. For example, the stent 26 or filter 36 may be advanced into the liner 10.

Figure 49:
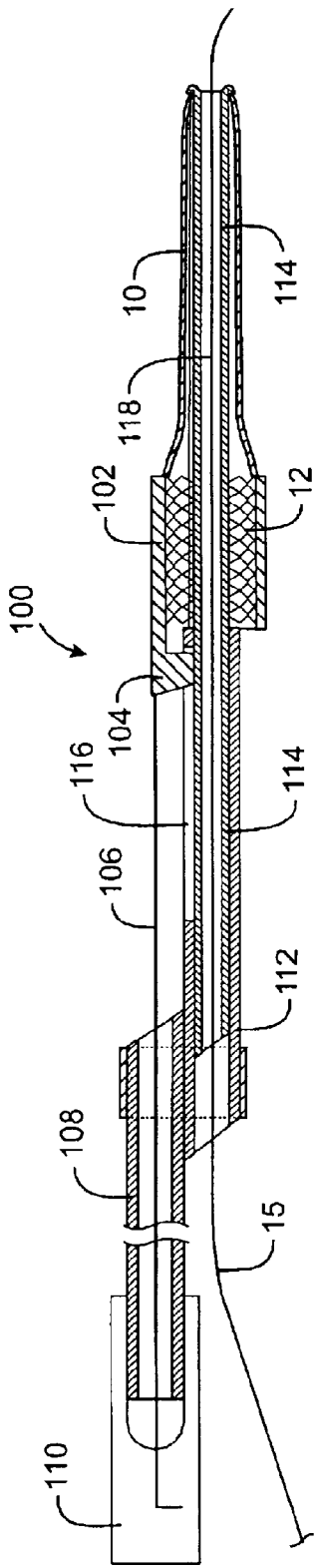
FIG. 49 shows yet another delivery catheter for the liner.

Referring to FIG. 49, another catheter 100 for delivering the liner 10 is shown. The catheter 100 has the self-expanding anchor 12 which is held in the collapsed position by a collar 102. An arm 104 is attached to the collar 102 which in turn is attached to a first core-wire 106. The first core wire 106 passes through a shaft 108 which has a handle 110 mounted to the proximal end. The handle 110 is retracted to pull the core wire 106, first arm 104 and collar 102 for releasing the self-expanding anchor 12.

A tube 112 is fused to the shaft 108 and an inner tube 114 is attached to the tube 114. The arm 104 travels in a slot 116 in the tube 114 to stabilize retraction of the collar 102. The tube 112 and inner tube 114 form a lumen 118 through which the guidewire 15 passes.

Figure 50:
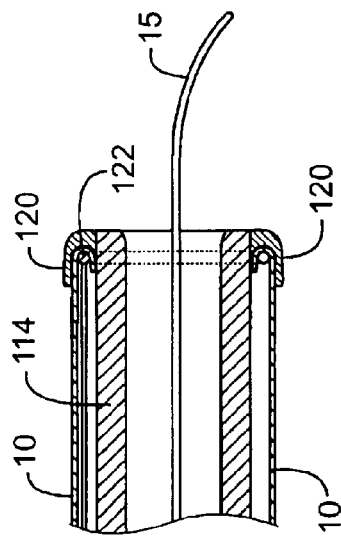
FIG. 50 shows a distal end of the liner trapped in a fold.

Referring to FIG. 50, the distal end of the liner 10 is locked into a fold 120 at the end of the inner tube 114. A wire loop 122 holds the liner 10 in the fold 120. The wire loop 122 is preferably attached to the collar 102 with a wire 124 embedded in the collar 102. The wire loop 122 is retracted together with the collar 102 so that the distal end of the liner 10 is released as the collar 102 is retracted. The wire loop 122 is preferably a 0.005 inch diameter stainless steel wire. The fold 120 is preferably made of silicone although other suitable materials may be used. The shaft 108 is preferably made of stainless steel hypotube having a wall thickness of about 0.005 inch and an outer diameter of about 0.024 inch. The tube 112 is preferably made of linear low density polyethylene having a wall thickness of about 0.004 inch and an outer diameter of about 0.040 inch. The inner tube 114 is preferably made of polyimide having a thickness of 0.0005 inch and an outer diameter of about 0.022 inch. The liner 10 is deployed and used in substantially the same manner as described above and the discussion above is applicable here.

Figure 52:
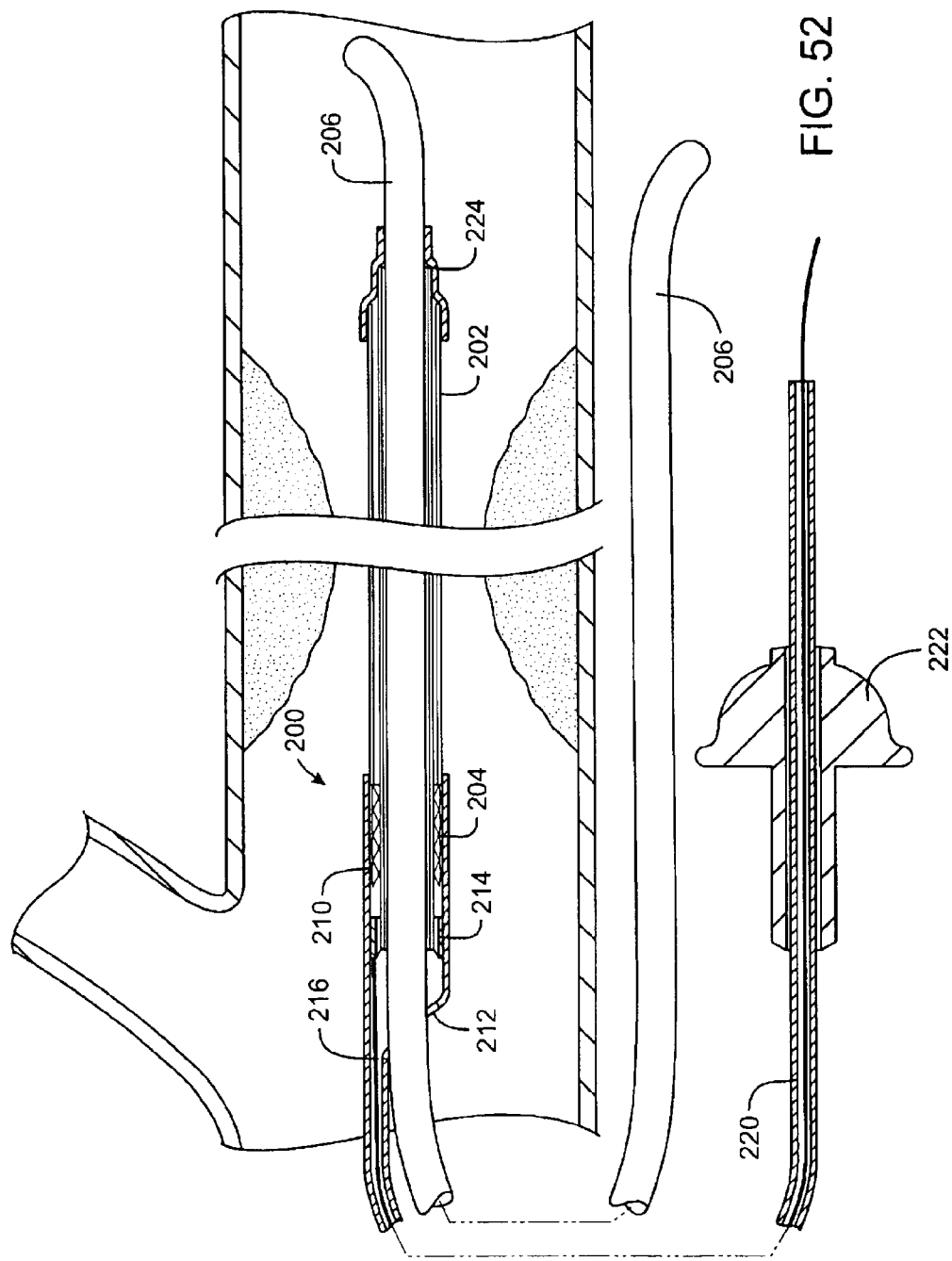
FIG. 52 shows still another liner in accordance with the present invention.

Referring to FIG. 52, yet another device 200 is shown. The device has a liner 202 and an anchor 204 which may be any liner or anchor described herein or any other suitable anchor or liner. The anchor 204 is attached to the proximal end of the liner 200 in any suitable manner such as with an adhesive such as a UV curable polyurethane. As with any of the liners described herein, the liner 200 and anchor 204 may have any of the dimensions and features described herein and may be used in any manner described herein without departing from the scope of the invention. The device 200 is advanced over a guidewire 206 which preferably has a diameter of 0.018 inch but may be any size. The guidewire 206 passes through a guidewire tube 208 which is preferably a polyimide tube having an inner diameter of 0.020 inch and a wall thickness of about 0.001 inch.

The anchor 204 is held in the collapsed position of FIG. 52 by a retention element 210 which has a size of about 4–8 French and preferably about 6 Fr. The retention element 210 has a length of 0.1–1.0 inch and more preferably 0.200–0.600 inch. A proximal end of the retention collar 210 has an opening 212 to receive the guidewire 208.

A bumper 214 is contained within the retention element 210 and is used to release the anchor 204 from the retention element 210 in the manner described below. An elongate element 216, such as a cable 218, is coupled to the bumper 214 for manipulating the bumper 214. The elongate element 216 passes through an actuator tube 220 coupled to the retention element 210. The actuator tube 220 is relatively small and has a size of no more than 0.030 inch and preferably no more than 0.025 inch. The elongate element 216 and actuator tube 220 are coupled to an actuator 222 for manipulating the bumper 214. The actuator 222 is shown schematically and can be formed in any suitable manner to provide relative movement as is known in the art. The bumper 214 is attached to the guidewire tube 208 so that the guidewire tube 208 moves with the bumper 214 in the manner described below. The bumper 214 is preferably a section of hypotube having an outer diameter suitable to slide within the retention element 210.

The distal end of the liner 200 is trapped by a tip cover 224 which is preferably made of isoprene such as CHRONOPRENE sold by CardioTech. Of course, any other suitable material may be used. The tip cover 224 has an inner diameter which is somewhat smaller, preferably about 0.0005–0.002 inch smaller, than the outer diameter of the guidewire tube 208. In this manner, the tip cover 224 applies a modest compressive force to the distal end of the liner 202 to hold the liner 202 in the collapsed position. The tip cover 224 lies partially over the guidewire tube 208 and partially over the liner 202. The tip cover 224 may be bonded to the distal end of the guidewire tube 208 to prevent release of the tip cover 224. Although the tip cover 2224 is preferred, any other mechanism for holding the sleeve in the collapsed position may be used including those described herein.

Figure 53:
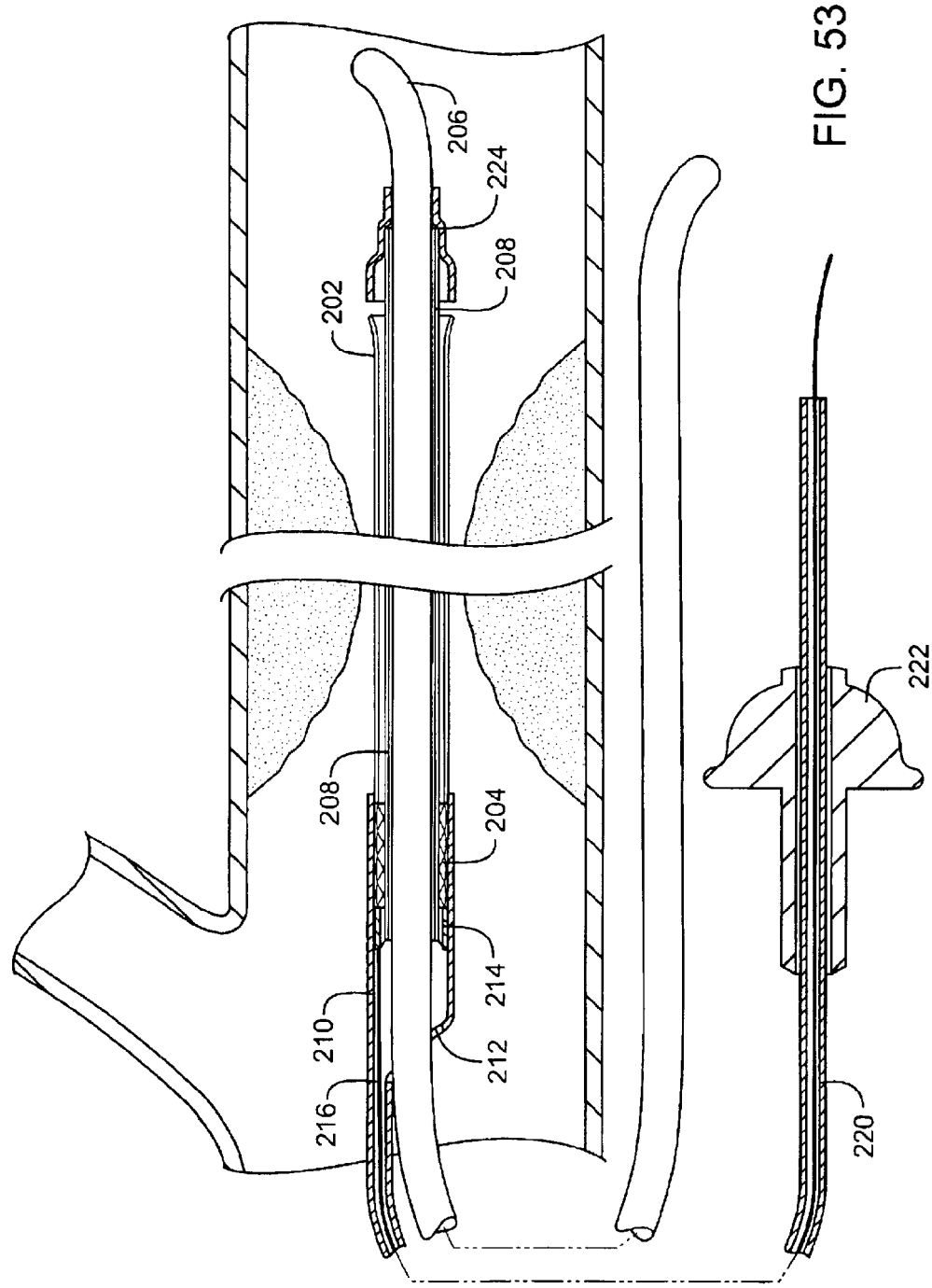
FIG. 53 shows the liner of FIG. 52 with a bumper advanced adjacent to the anchor.
Figure 54A:
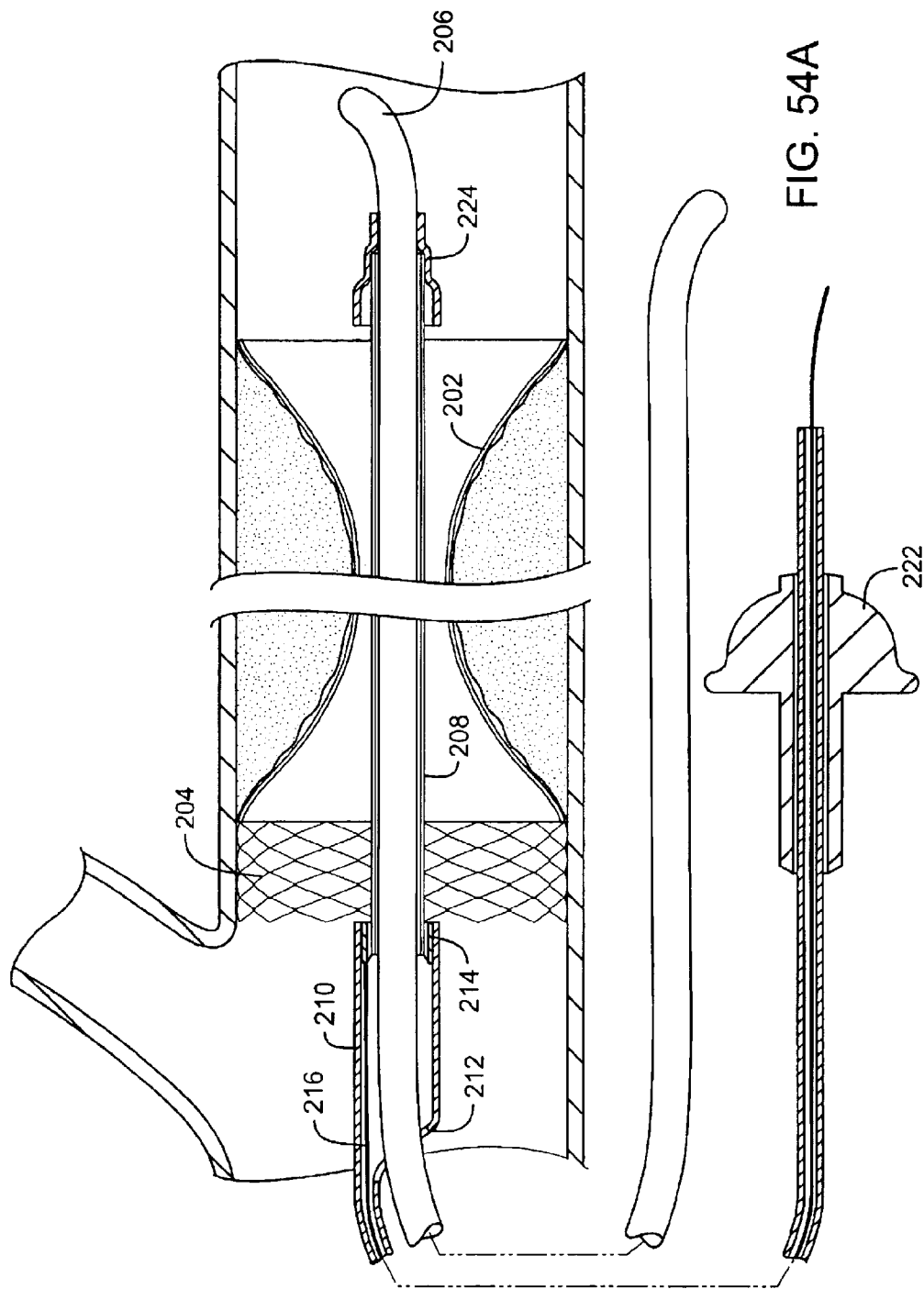
FIG. 54A shows the retention element retracted to expose the anchor and permit the anchor to expand.
Figure 54B:
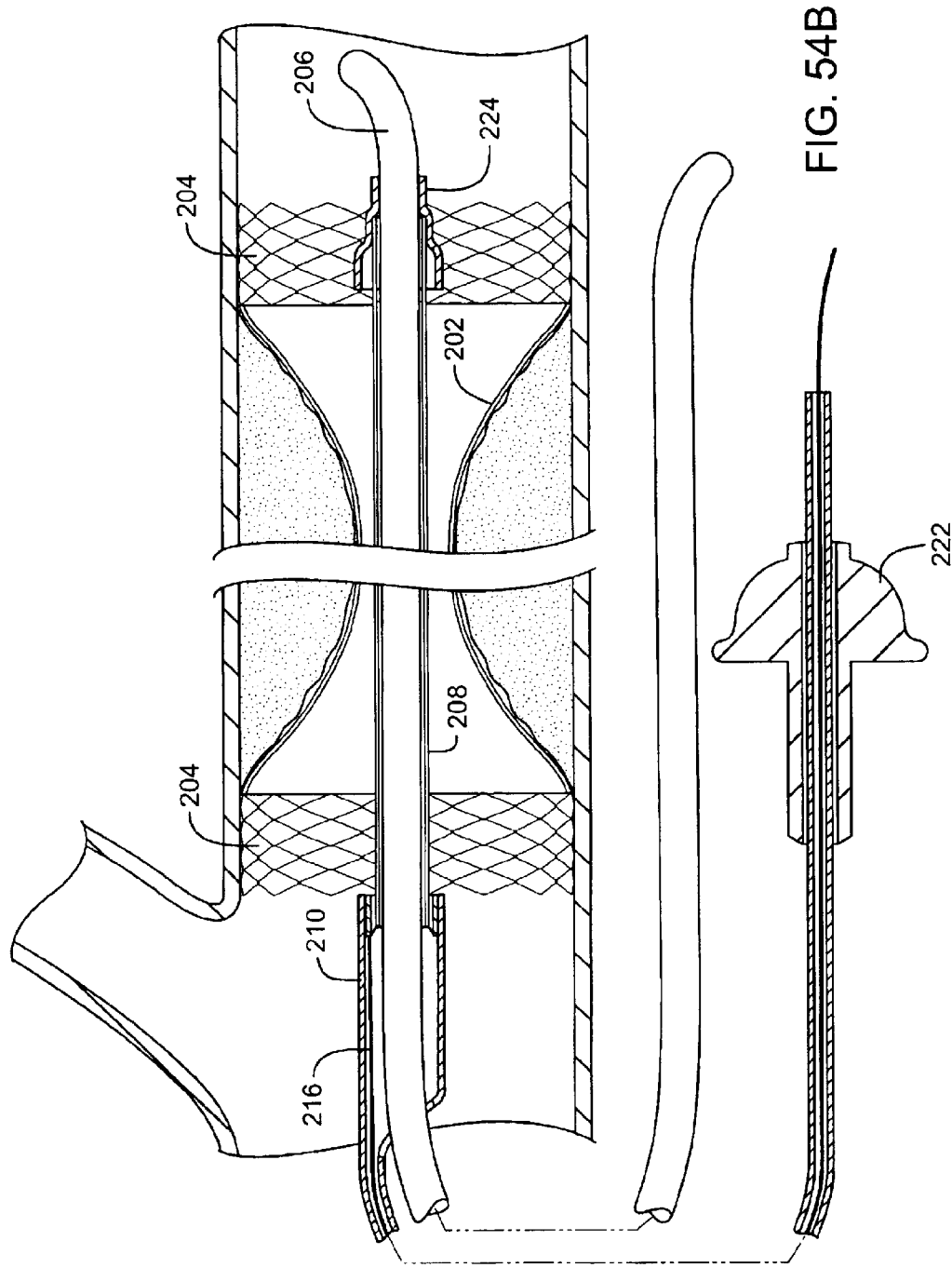
FIG. 54B shows the liner having anchors at both ends.

Use of the device 200 is now described with reference to FIGS. 52–54A. The liner 202 is advanced over the guidewire 206 to a treatment site such as the internal carotid artery. The treatment site may require any treatment described herein including opening of a narrowed portion of a blood vessel as shown in FIG. 52. Once the device 200 is in position, the bumper 214 is advanced adjacent to the anchor 204 as shown in FIG. 53 by manipulating the elongate element 216 with the actuator 222. As the bumper 214 is advanced, the tip cover 224 is moved distally out of engagement with the liner 202 to release the distal end of the liner 202. The retention element 210 is then withdrawn while holding the bumper 214 in the same position to expose the anchor 204 and permit the anchor to expand as shown in FIG. 54A. The liner 202 is now in position to receive another medical device as described above. For example, a balloon could be advanced into the liner 202 and expanded to open the narrowed region. Alternatively, or in addition to use of the balloon, a stent may be advanced into the liner 202 and expanded for opening the narrowed portion of the vessel.

As mentioned above, any of the liners described herein may have the anchor at both ends (FIG. 54B) or throughout the liner (FIG. 54C) without departing from various aspects of the present invention. The anchor preferably has a relatively low opening force and does not significantly open the narrowed portion of the vessel (FIG. 54C). It is believe that barotrauma, or pressure-induced trauma, may contribute to restenosis when using conventional devices. The present invention provides low opening force thereby reducing barotrauma as compared to conventional methods and devices.

Figure 55:
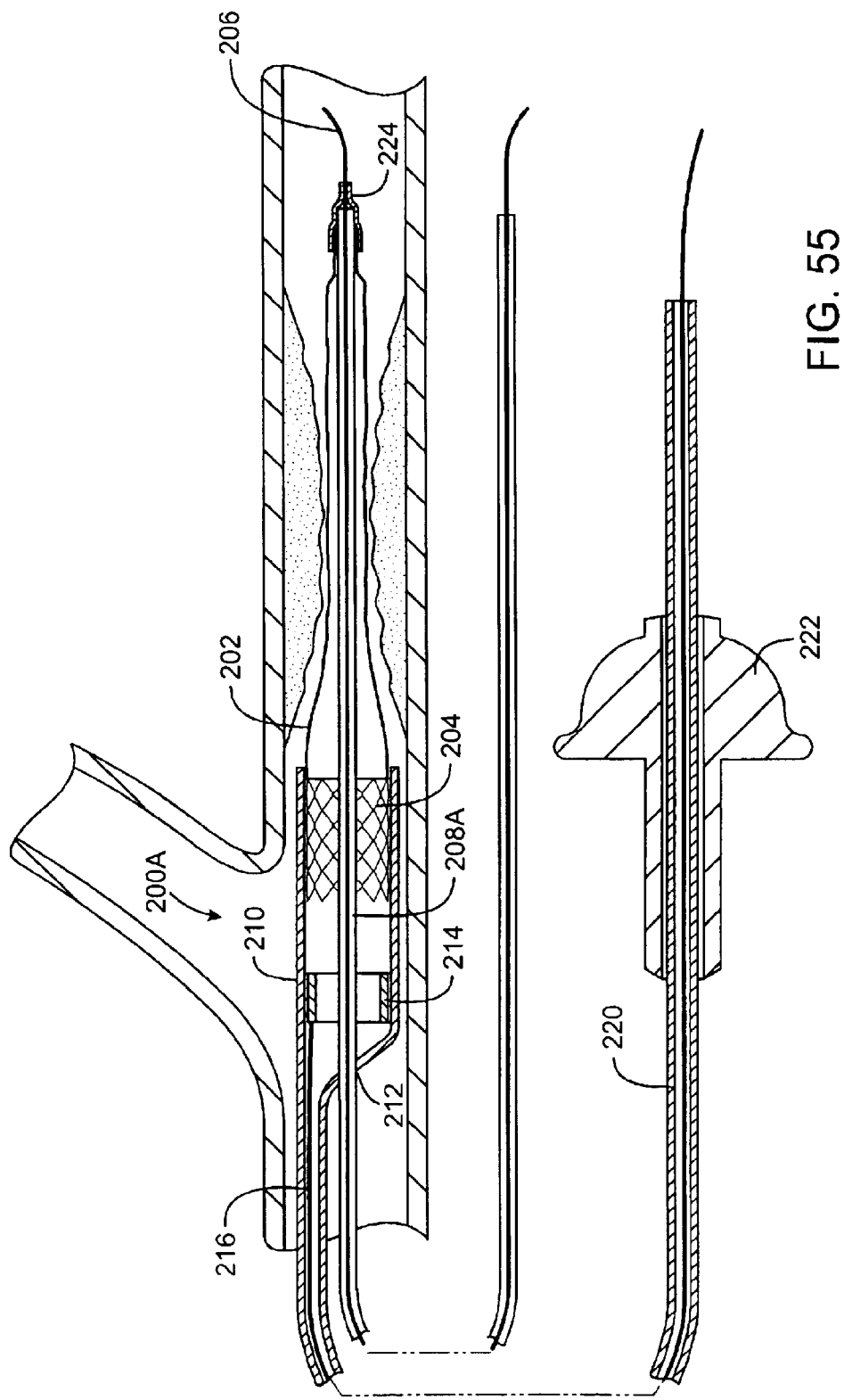
FIG. 55 shows an alternative embodiment of the device of FIG. 52.

Referring to FIG. 55, another device 200A is shown wherein the same or similar reference numbers refer to the same or similar structure. The guidewire 206 has been reduced in size for clarity. The device 200A has the liner 202 and the anchor 204 which may be any liner or anchor described herein and all features, dimensions, methods of use and advantages of the liners and anchors described herein are equally applicable here. The device 200A is similar in structure and use to the device 200 except that the guidewire tube 208A is not attached to the bumper 214. The guidewire tube 208A is separate from the bumper 214 so that bumper 214 can be moved independent of release of the distal end of the liner 202 with the tip cover 224.

The device 200A is used in substantially the same manner as the device 200 except that the guidewire lumen 208A and the retention element 210 are advanced together to the target site. The user may then advance the bumper 214 adjacent to the anchor 204 before releasing the distal end of the liner 202. The anchor is then released by withdrawing the retention element 210. The distal end of the liner 200A is then released by simply advancing the guidewire tube 208A. Alternatively, the user may release the distal end of the liner 200A before advancing the bumper 214.

Figure 56:
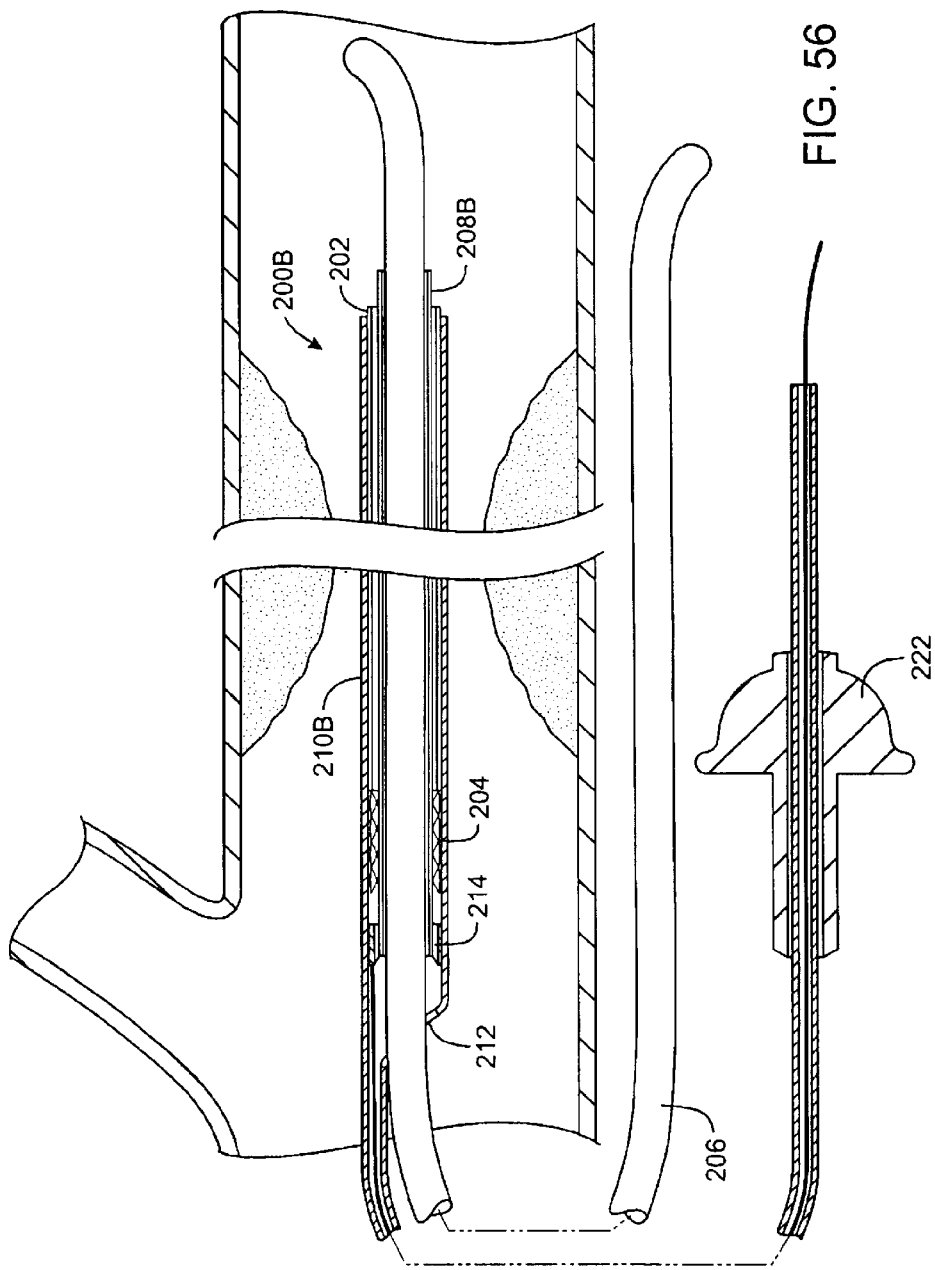
FIG. 56 shows another alternative embodiment of the device of FIG. 52.

Referring now to FIG. 56, still another device 200B is shown wherein the same or similar reference numbers refer to the same or similar structure. The device 200B has the liner 202 and the anchor 204 which may be any liner or anchor described herein. The device 200B is similar in structure and use to the device 200 except that a retention element 210B extends over the liner 202 to hold the liner 202 in the collapsed position. The device 200B is used in the same manner as the device 200.

Figure 57:
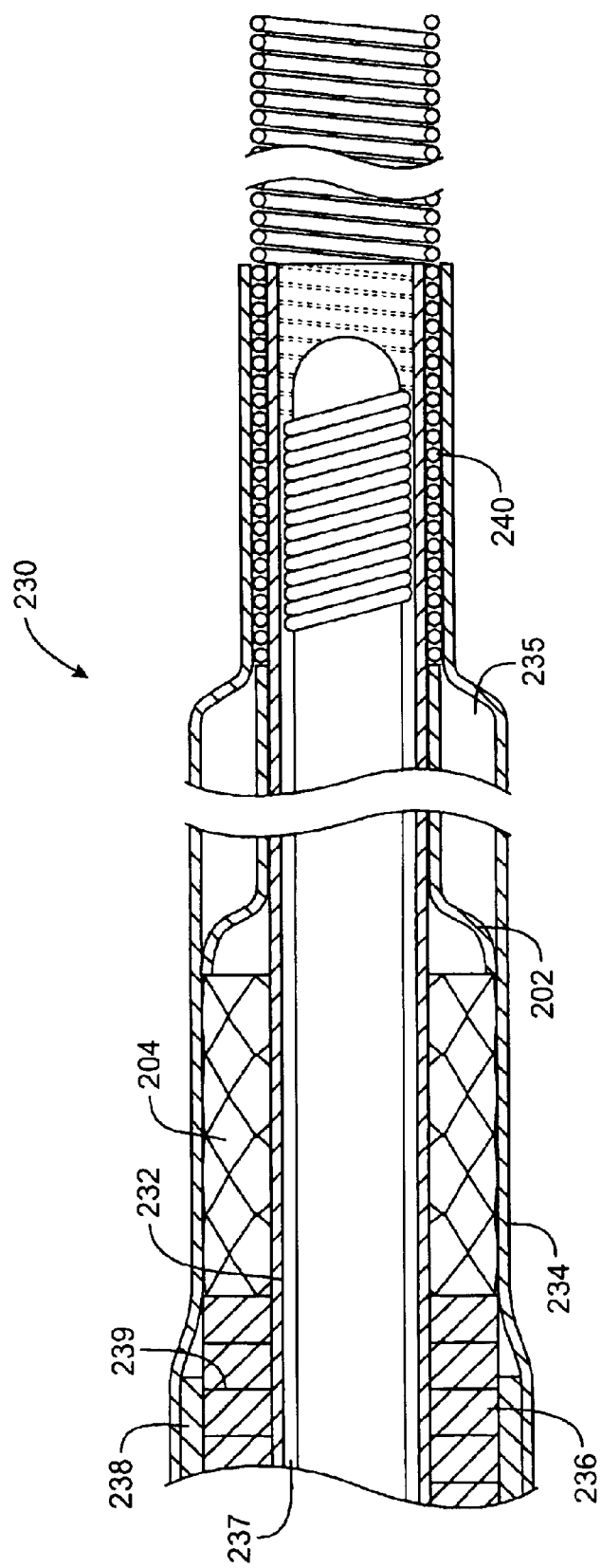
FIG. 57 shows yet another liner in accordance with the present invention.

Referring now to FIG. 57, the distal end of another device 230 is shown. The device 230 has the liner 202 and the anchor 204 which may be any liner or anchor described herein and all features, dimensions and advantages of the liners and anchors described herein are equally applicable here. The liner 202 is trapped between an inner layer 232 and an outer layer 234. The liner 202 occupies a space 235 between the inner and outer layers 232, 234 and the manner in which the liner 202 is collapsed is not shown for clarity. The liner 202 is preferably collapsed in the manner described above or another suitable method.

The inner and outer layers 232, 234 are relatively thin and flexible. Specifically, the inner and outer layers 232, 234 have a thickness of no more than 0.002 inch and more preferably no more than 0.001 inch. The inner layer 232 is preferably a shrink tube having a thickness of about 0.0005–0.002 inch, preferably about 0.0005 inch, and an outer diameter of 0.021 inch. The outer layer 234 is preferably a PET shrink tube having a 0.001 inch thickness and an outer diameter of 0.0047 inch. The outer layer 234 preferably applies a modest compressive force to the liner 202 to hold the liner 202 in the collapsed position. To provide such a force, the outer layer 234 is sized about 0.0005–0.002 inch smaller than the collapsed diameter of the liner. The outer layer 234 preferably has an outer diameter of less than 0.050 inch and more preferably less than 0.045 inch and most preferably about 0.043 inch. The inner and outer layers 232, 234 preferably extend to the proximal end of the device. The inner and outer layers 232, 234 advantageously hold the liner 202 in the collapsed position of FIG. 57 while still maintaining sufficient flexibility to pass through small, tortuous vessels.

The liner 202 may be collapsed in any manner described herein. For example, the liner 202 may have the folds 14 (FIGS. 7–12) which are wrapped around one another. The folds 14 may be formed in any suitable manner and a preferred manner is to tension the liner 202 to naturally create the folds 14. When the liner 202 is tensioned, the liner 202 naturally forms about 10–20 folds 14 which are then wrapped to collapse the liner 202 in the manner shown in FIGS. 7–12. The liner 202 is collapsed to the preferred dimensions described above, for example, the liner may have the length, collapsed length, thickness, and expanded sizes described above.

The inner layer 232 is preferably bonded to an inner element 236 and the outer layer 234 is preferably bonded to an outer element 238. The inner and outer elements 236, 238 are preferably tubes but may take other suitable shapes and configurations. The inner and outer elements 236, 238 can be moved relative to one another to retract the outer layer 234 and release the anchor 204 and liner 202 as described below. The outer element 238 may be made of any suitable material and a preferred material is a polyimide tube having a thickness of about 0.003 inch and an outer diameter of about 0.039 inch. Although it is preferred to provide the outer element 238, the device may also be practiced without the outer element 236 and only the outer layer 234 without departing from the scope of the invention.

The inner element 236 provides a lumen 237 for receiving the guidewire. The lumen 237 preferably has a diameter of 0.010–0.030 inch, more preferably 0.015–0.025 inch and most preferably about 0.017 inch. The inner element 236 is preferably polyetherether ketone having a thickness of about 0.007 inch and an outer diameter of about 0.035 inch. The guidewire 206 may have any suitable size and s preferably a 0.014 inch guidewire. The inner element 236 preferably has a spiral cut 39 near the distal end to enhance flexibility and prevent kinking. The spiral cut 239 forms sections having a length of about 0.003–0.004 inch.

As mentioned above, the device, and in particular the liner 202 and the anchors 204, may take any of the dimensions, features and advantages of the other liners and anchors described herein. The device may also have the following dimensions. The diameter of the outer layer extending over the liner and anchor is preferably no more than 0.055 inch, more preferably no more than 0.050 inch and most preferably no more than 0.040 inch. The outer layer 232, liner 202 and inner layer 234 together form a relatively small radial thickness, preferably about 0.007–0.015 and more preferably 0.007–0.013 inch.

The inner and outer layers 232, 234 preferably continue beyond the distal end of the liner and a radiopaque coil 240, such as a platinum coil, extends between and beyond the layers 232, 234. The coil 240 preferably has a diameter of 0.003 inch and is wound to a diameter of about 0.018 inch. The coil 240 extends for a total length of about 0.300 inch with an exposed length beyond the inner and outer layers 232, 234 of about 0.250 inch. The outer layer 234 tapers down distal to the liner 202 to a diameter of less than 0.035, more preferably less than 0.030 and most preferably about 0.024 inch.

Figure 58:
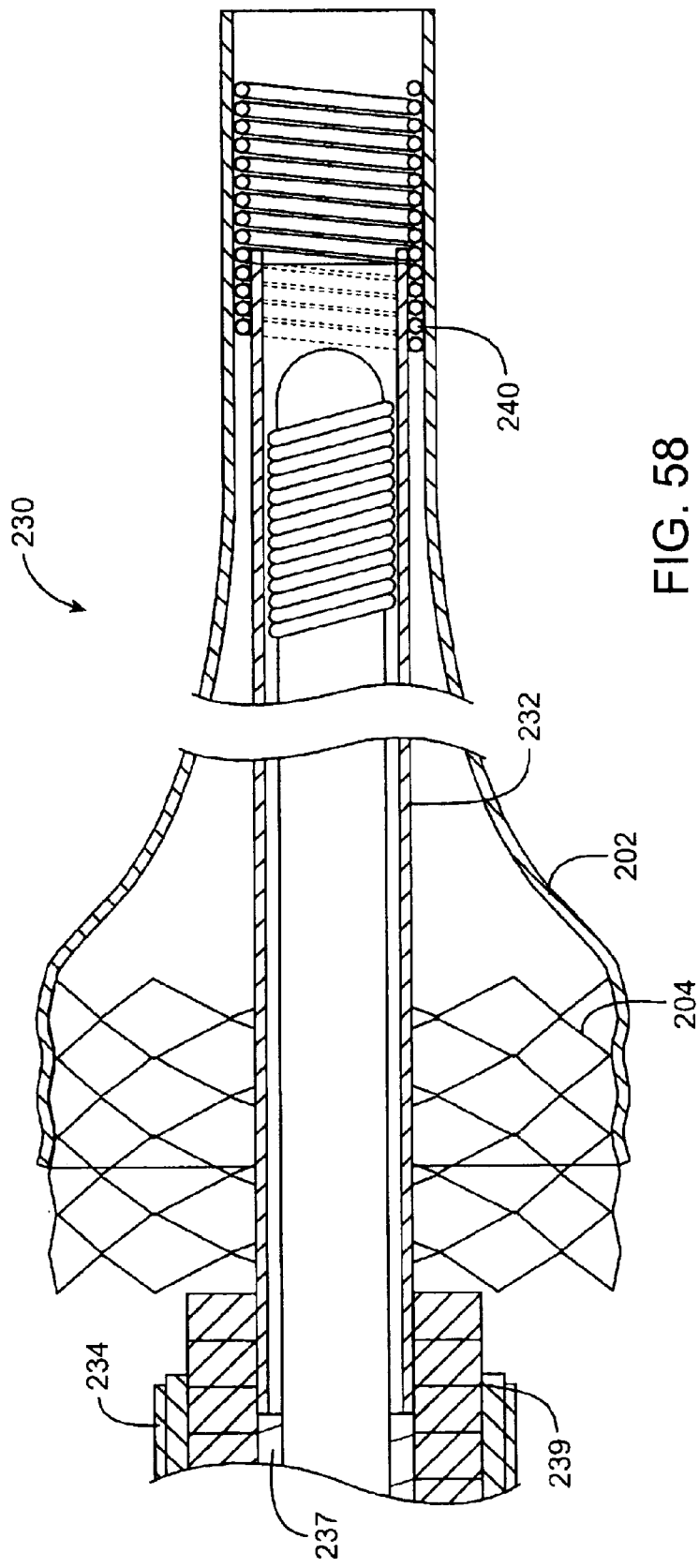
FIG. 58 shows the device of FIG. 57 with the anchor expanded and the liner released.

Use of the device 230 is now described. The device 230 is advanced through the vasculature to a treatment site. The outer layer 238 is then retracted while holding the inner element 236 to expose the liner 202 and anchor 204 thereby permitting the anchor 204 to expand as shown in FIG. 58. As the anchor 204 expands, the liner 202 is released and expands together with the anchor 204. After deployment of the liner 202, any medical device described herein, including a device to open a narrowed region of a blood vessel such as a stent, may be advanced into or through the liner 202.

Figure 59:
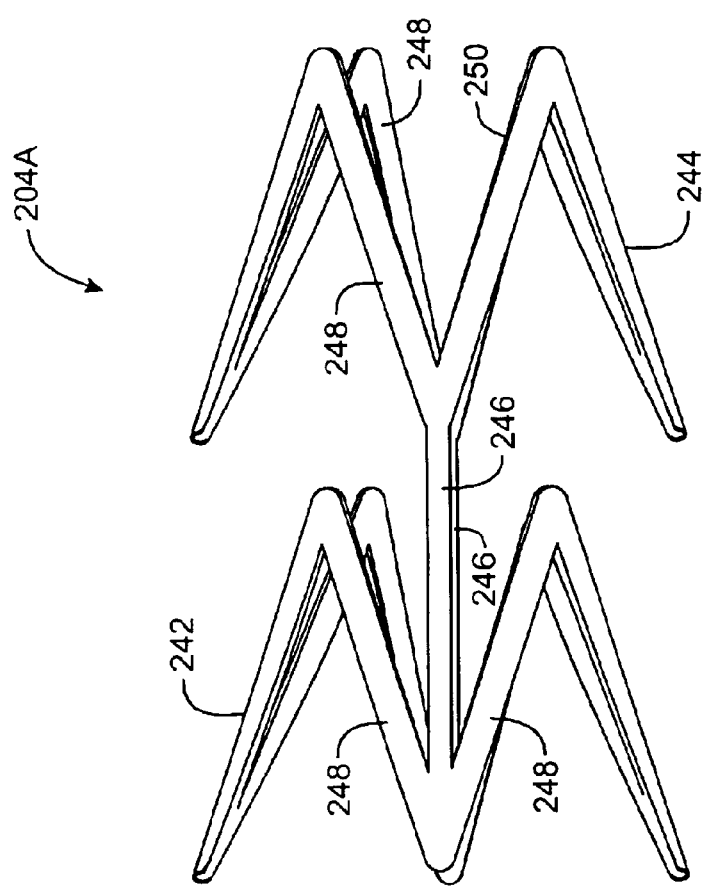
FIG. 59 shows a preferred anchor in an expanded position.

Referring to FIG. 59, a preferred anchor 204A is shown in an expanded and position. As mentioned herein, any of the anchors may be used with any of the liners without departing from the scope of the invention. The anchor 204A is formed by laser cutting or etching a tube which is preferably made of a superelastic material such as nitinol. As an example, the anchor 204A may have an outer diameter of about 0.060 inch and a wall thickness of about 0.006 inch. The tube is cut or etched to form first and second sections 242, 244 connected by longitudinal connecting elements 246. Each section 242, 244 is formed by struts 248 connected end to end in a zig-zag pattern to form a closed loop 250. As mentioned above, the anchor 204A may be similar to a stent or any other suitable device for holding the liner 202 at the desired location. The preferred anchor 204A of the present invention does, however, differ from conventional stents as described below.

The preferred anchor 204A of FIG. 59 is shorter than conventional stents to provide reduced interference with branch vessels. The anchor 204A has a length of less than 15 mm, more preferably less than 10 mm when expanded. The relatively small length provides flexibility to access small, tortuous vessels. The anchor 204A can be somewhat short since the anchor 204A is simply holding the liner in place during introduction of other devices, such as the stent, into the liner 202. The anchor 204A also preferably has a relatively low opening force since the anchor 204A is not intended to provide significant opening of the vessel. Although the anchor 204A is shorter and has a lower opening force than a conventional stent, the anchor 204A may differ from conventional stents in more or fewer ways without departing from various aspects of the present invention.

Figure 51:
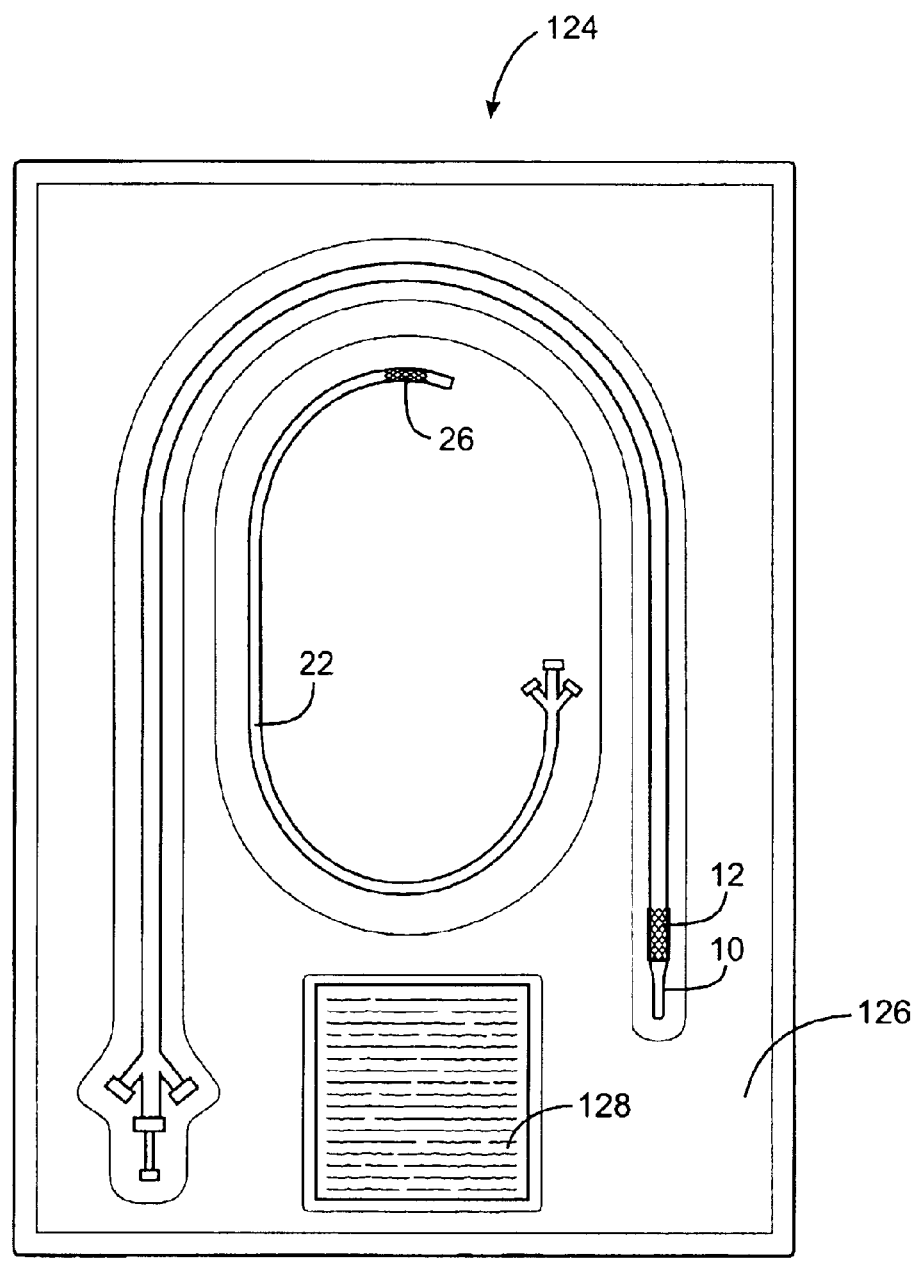
FIG. 51 shows a kit having devices and instructions for use in accordance with the present invention.

The present invention is also directed to kits 124 which include various assemblies as described above. For example, the kit 124 may include the liner 10, delivery catheter 22 and instructions for use 128 setting forth any of the methods described herein as shown in FIG. 51. The kits may, of course, also include the stent(s) 26, anchors 12 and stent delivery catheter(s) 22 and/or the filter 36 as well. The kits 124 will usually include a container 126, such as a pouch, tray, box, tube, or the like, which contains the devices as well as the instructions for use 128. The instructions for use 128 may be set forth on a separate instructional sheet within the package or printed in whole or in part on the packaging itself. Optionally, other system components useful for performing the methods of the present invention could be provided within the kit 124, including guidewires, introductory sheaths, guiding catheters, and the like. Any of the devices described herein may form a kit with instructions setting forth a method of the present invention.

While the above is a complete description of the preferred embodiments of the invention, various alternatives, modifications, and equivalents may be used. Therefore, the above description should not be taken as limiting the scope of the invention which is defined by the appended claims. For example, any of the delivery catheters may have a balloon for occluding the vessel while delivering the liner or advancing the device through the liner and any of the liners may have perforations to filter blood or may be made of a tightly woven material. Furthermore, the preferred dimensions described herein with respect to any of the embodiments is equally applicable to other embodiments. Finally, all aspects of the present invention may also be practiced with the delivery of drugs, radiation and drugs for anti-restenosis and anti-platelet adhesion.

What is claimed is:

1. A device for lining a vessel, comprising:
    an expandable anchor movable from a collapsed shape to an expanded shape;
    a liner attached to the anchor and extending from an end of the anchor;
    an inner layer, the liner being mounted over the inner layer;
    an outer layer extending over the liner and the anchor, the outer layer being retracted to expose the liner when the outer layer is moved proximally relative to the inner layer; and
    a radiopaque coil extending beyond the distal end of the liner and the inner and outer layers, the radiopague coil also being positioned at least partially between the inner and outer layers.

2. The device of claim 1 wherein:
    the outer layer holds the anchor in the collapsed position.

3. The device of claim 1 wherein:
    the outer layer has a thickness of 0.0005–0.002 inch.

4. The device of claim 1 wherein:
    the outer layer stretches over a tapered portion, the outer layer stretching as it passes over the tapered portion when the outer layer is moved proximally relative to the inner layer.

5. The device of claim 1 further comprising:
    an inner element positioned beneath the liner and the anchor, the inner layer being attached to the inner element.

6. The device of claim 5, wherein:
    the inner layer has a thickness of 0.0005–0.002 inch.

7. The device of claim 1 wherein:
    the outer layer has a diameter of no more than 0.055 inch when in the collapsed position.

8. The device of claim 1 wherein:
    the outer layer has a diameter of no more than 0.050 inch when in the collapsed position.

9. The device of claim 1 wherein:
    the outer layer applies a compressive force to the liner to hold the liner in the collapsed position.

10. The device of claim 1 wherein:
    the outer layer lies directly over the anchor and holds the anchor in the collapsed position, the outer layer being retracted by an outer element to expose the anchor and permit the anchor to move to the expanded position.

11. The device of claim 1 wherein:
the liner is collapsed by forming a number of folds.

12. The device of claim 1 wherein:
the liner is made of expanded PTFE.

13. The device of claim 1 wherein:
the inner and outer layers extend beyond a distal end of the liner, the outer layer tapering distally and being flexible enough to expand over the tapered section when the outer layer is retracted relative to the inner layer.

14. The device of claim 1 wherein:
the inner liner is attached to an inner element, the inner element engaging the anchor to hold the anchor when the outer layer is retracted relative to the inner layer.

15. The device of claim 14, wherein:
the inner element is spiral cut at a distal end.

16. The device of claim 15, wherein:
the inner element has a lumen for receiving a guidewire, the lumen having a diameter of 0.015–0.25 inch.

17. The device of claim 1 wherein:
the anchor has a length of less than 15 mm when collapsed.

18. A method of lining a vessel, comprising the steps of:
providing an expandable anchor, a liner, an inner layer, and an outer layer, the anchor and liner being movable from a collapsed shape to an expanded shape, the liner being attached to the anchor and extending from an end of the anchor, the outer layer being slidable relative to the inner layer, the outer layer extending over the liner and the anchor in the collapsed position, the radiopaque coil extending beyond the distal end of the liner and the inner and outer layers, the radiopaque coil being positioned at least partially between the inner and outer layers;
advancing a medical device to a treatment site;
retracting the outer layer to expose the liner and the anchor to permit the anchor to expand; and
advancing the medical device into the liner after the retracting step.

19. The method of claim 18 wherein:
the providing step is carried out with the outer layer holding the anchor and the liner in the collapsed position.

20. The method of claim 18 wherein:
the providing step is carried out with the outer layer having a thickness of 0.0005–0.002 inch.

21. The method of claim 18 wherein:
the providing step is carried out with the outer layer having a tapered portion when the anchor is in the collapsed position; and
the retracting step is carried out with the outer layer stretching over the tapered portion as it passes over the tapered portion.

22. The method of claim 21, wherein:
the providing step is carried out with the inner layer having a thickness of 0.0005–0.002 inch.

23. The method of claim 18 wherein:
the providing step is carried out with the outer layer having a diameter of no more than 0.050 inch when in the collapsed position.

24. The method of claim 18 wherein:
the providing step is carried out with the outer layer having a diameter of no more than 0.045 inch when in the collapsed position.

25. The method of claim 18 wherein:
the providing step is carried out with the outer layer lying directly over the anchor to hold the anchor in the collapsed position;
the retracting step being carried out so that the outer layer is retracted to expose the anchor and permit the anchor to expand.

26. The method of claim 18 wherein:
the providing step is carried out with the liner collapsed by forming a number of folds which are folded around one another.

27. The method of claim 18 wherein:
the providing step is carried out with the liner being made of expanded PTFE.

28. The method of claim 18, wherein:
the advancing step is carried out with the medical device being a medical device selected from the group consisting of a stent, an angioplasty balloon, a filter, a drug delivery device, and an atherectomy device.

29. The method of claim 18 wherein:
the providing step is carried out with the inner layer being attached to an inner element; and
the retracting step is carried out with the inner element contacting the anchor to hold the anchor in place while retracting the outer layer.

30. The method of claim 29, wherein:
the providing step is carried out with the inner element having a lumen for receiving a guidewire, the lumen having a diameter of 0.015–0.25 inch.

31. The method of claim 18 wherein:
the providing step is carried out with the outer layer attached to an outer element; and
the retracting step is carried out with the outer element being retracted with the outer layer.

32. The method of claim 18 wherein:
the providing step is carried out with the anchor having a length of less than 15 mm when collapsed.

33. A method of opening a narrowed region in a blood vessel, comprising the steps of:
providing a liner movable from a collapsed condition to an expanded condition;
advancing the liner to a narrowed region of a blood vessel with the liner in the collapsed position;
passing at least a portion of the liner through the narrowed region of the blood vessel in the collapsed position;
moving a stent into the liner after the passing step so that the stent is also positioned in the narrowed region of the blood vessel; and
expanding the stent after the moving step so that the stent expands the liner and opens the narrowed region of the vessel.

34. The method of claim 33, wherein:
the advancing and passing steps are carried out with the blood vessel being a vessel selected from the group comprising the internal carotid artery and saphenous vein graft.

35. The method of claim 33, further comprising the step of:
expanding at least part of the liner before expanding the stent.

36. A device for lining a vessel, comprising:
An expandable anchor movable from a collapsed shape to an expanded shape;
a liner attached to the anchor and extending from an end of the anchor;

an inner layer, the liner being mounted over the inner layer; and an outer layer extending over the liner and the anchor, the outer layer being retracted to expose the liner when the outer layer is moved proximally relative to the inner layer, the outer layer stretching over a tapered portion, the outer layer stretching as it passes over the tapered portion when the outer layer is moved proximally relative to the inner layer;

wherein the inner layer is attached to an inner element, the inner element engaging the anchor to hold the anchor when the outer layer is retracted relative to the inner layer, the inner element being spiral cut at a distal end.

37. The device of claim 36 wherein:
the outer layer holds the anchor in the collapsed position.

38. The device of claim 36 wherein:
the outer layer has a thickness of 0.0005–0.002 inch.

39. The device of claim 36 further comprising:
an inner element positioned beneath the liner and the anchor, the inner layer being attached to the inner element.

40. The device of claim 39 wherein:
the inner layer has a thickness of 0.0005–0.002 inch.

41. The device of claim 36 wherein:
the outer layer has a diameter of no more than 0.055 inch when in the collapsed position.

42. The device of claim 36 wherein:
the outer layer has a diameter of no more than 0.050 inch when in the collapsed position.

43. The device of claim 36 wherein:
the outer layer applies a compressive force to the liner to hold the liner in the collapsed position.

44. The device of claim 36 wherein:
the outer layer lies directly over the anchor and holds the anchor in the collapsed position, the outer layer being retracted by an outer element to expose the anchor and permit the anchor to move to the expanded position.

45. The device of claim 36 wherein:
the liner is collapsed by forming a number of folds.

46. The device of claim 36 wherein:
the liner is made of expanded PTFE.

47. The device of claim 36 further comprising:
radiopaque coil extending beyond the distal end of the liner and being positioned at least partially between the inner and outer layers.

48. The device of claim 47, wherein:
the radiopaque coil extends beyond the distal end of the inner and outer layers.

49. The device of claim 36, wherein:
the inner and outer layers extend beyond a distal end of the liner, the outer layer tapering distally and being flexible enough to expand over the tapered section when the outer layer is retracted relative to the inner layer.

50. The device of claim 36, wherein:
the inner element has a lumen for receiving a guidewire, the lumen having a diameter of 0.015–0.25 inch.

51. The device of claim 36, wherein:
the anchor has a length of less than 15 mm when collapsed.

52. A device for lining a vessel, comprising:
an expandable anchor movable from a collapsed shape to an expanded shape;
a liner attached to the anchor and extending from an end of the anchor;

an inner layer, the liner being mounted over the inner layer; and an outer layer extending over the liner and the anchor, the outer layer being retracted to expose the liner when the outer layer is moved proximally relative to the inner layer, the inner and outer layers extending beyond a distal end of the liner, the outer layer tapering distally and being flexible enough to expand over the tapered section when the outer layer is retracted relative to the inner layer;

wherein the inner layer is attached to an inner element, the inner element engaging the anchor to hold the anchor when the outer layer is retracted relative to the inner layer, the inner element being spiral cut at a distal end.

53. The device of claim 52, wherein:
the outer layer holds the anchor in the collapsed position.

54. The device of claim 52, wherein:
the outer layer has a thickness of 0.0005–0.002 inch.

55. The device of claim 52, wherein:
the outer layer stretches over a tapered portion, the outer layer stretching as it passes over the tapered portion when the outer layer is moved proximally relative to the inner layer.

56. The device of claim 52, further comprising:
an inner element positioned beneath the liner and the anchor, the inner layer being attached to the inner element.

57. The device of claim 56, wherein:
the inner layer has a thickness of 0.0005–0.002 inch.

58. The device of claim 52, wherein:
the outer layer has a diameter of no more than 0.055 inch when in the collapsed position.

59. The device of claim 52, wherein:
the outer layer has a diameter of no more than 0.050 inch when in the collapsed position.

60. The device of claim 52, wherein:
the outer layer applies a compressive force to the liner to hold the liner in the collapsed position.

61. The device of claim 52, wherein:
the outer layer lies directly over the anchor and holds the anchor in the collapsed position, the outer layer being retracted by an outer element to expose the anchor and permit the anchor to move to the expanded position.

62. The device of claim 52, wherein:
the liner is collapsed by forming a number of folds.

63. The device of claim 52, wherein:
the liner is made of expanded PTFE.

64. The device of claim 52, further comprising:
a radiopaque coil extending beyond the distal end of the liner and being positioned at least partially between the inner and outer layers.

65. The device of claim 64, wherein:
the radiopaque coil extends beyond the distal end of the inner and outer layers.

66. The device of claim 52, wherein:
the inner element has a lumen for receiving a guidewire, the lumen having a diameter of 0.015–0.25 inch.

67. The device of claim 52, wherein:
the anchor has a length of less than 15 mm when collapsed.

68. A device for lining a vessel, comprising:
an expandable anchor movable from a collapsed shape to an expanded shape;
a liner attached to the anchor and extending from an end of the anchor;

an inner layer, the liner being mounted over the inner layer;

an outer layer extending over the liner and the anchor, the outer layer being retracted to expose the liner when the outer layer is moved proximally relative to the inner layer; and an inner element attached to the inner layer, the inner element engaging the anchor to hold the anchor when the outer layer is retracted relative to the inner layer, the inner element being spiral cut at a distal end.

69. The device of claim 68, wherein:

the outer layer holds the anchor in the collapsed position.

70. The device of claim 68, wherein:

the outer layer has a thickness of 0.0005–0.002 inch.

71. The device of claim 68, wherein:

the outer layer stretches over a tapered portion, the outer layer stretching as it passes over the tapered portion when the outer layer is moved proximally relative to the inner layer.

72. The device of claim 68, wherein:

the inner layer has a thickness of 0.0005–0.002 inch.

73. The device of claim 68, wherein:

the outer layer has a diameter of no more than 0.055 inch when in the collapsed position.

74. The device of claim 68, wherein:

the outer layer has a diameter of no more than 0.050 inch when in the collapsed position.

75. The device of claim 68, wherein:

the outer layer applies a compressive force to the liner to hold the liner in the collapsed position.

76. The device of claim 68, wherein:

the outer layer lies directly over the anchor and holds the anchor in the collapsed position, the outer layer being retracted by an outer element to expose the anchor and permit the anchor to move to the expanded position.

77. The device of claim 68, wherein:

the liner is collapsed by forming a number of folds.

78. The device of claim 68, wherein:

the liner is made of expanded PTFE.

79. The device of claim 68, further comprising:

a radiopaque coil extending beyond the distal end of the liner and being positioned at least partially between the inner and outer layers.

80. The device of claim 79, wherein:

the radiopaque coil extends beyond the distal end of the inner and outer layers.

81. The device of claim 68, wherein:

the inner and outer layers extend beyond a distal end of the liner, the outer layer tapering distally and being flexible enough to expand over the tapered section when the outer layer is retracted relative to the inner layer.

82. The device of claim 68, wherein:

the inner element has a lumen for receiving a guidewire, the lumen having a diameter of 0.015–0.25 inch.

83. The device of claim 68, wherein:

the anchor has a length of less than 15 mm when collapsed.

84. A device for lining a vessel, comprising:

an expandable anchor movable from a collapsed shape to an expanded shape;

a liner attached to the anchor and extending from an end of the anchor;

an inner layer, the liner being mounted over the inner layer;

an outer layer extending over the liner and the anchor, the outer layer being retracted to expose the liner when the outer layer is moved proximally relative to the inner layer; and a radiopaque coil extending beyond the distal end of the liner and also being positioned at least partially between the inner and outer layers, wherein the inner liner is attached to an inner element, the inner element engaging the anchor to hold the anchor when the outer layer is retracted relative to the inner layer, the inner element being spiral cut at a distal end.

85. The device of claim 84, wherein:

the inner element has a lumen for receiving a guidewire, the lumen having a diameter of 0.015–0.25 inch.

86. A device for lining a vessel, comprising:

an expandable anchor movable from a collapsed shape to an expanded shape;

a liner attached to the anchor and extending from an end of the anchor;

an inner layer, the liner being mounted over the inner layer;

an outer layer extending over the liner and the anchor, the outer layer being retracted to expose the liner when the outer layer is moved proximally relative to the inner layer, the outer layer stretching over a tapered portion, the outer layer stretching as it passes over the tapered portion when the outer layer is moved proximally relative to the inner layer; and a radiopaque coil extending beyond the distal end of the liner and being positioned at least partially between the inner and outer layers.

87. The device of claim 86, wherein:

the radiopaque coil extends beyond the distal end of the inner and outer layers.

88. A device for lining a vessel, comprising:

an expandable anchor movable from a collapsed shape to an expanded shape;

a liner attached to the anchor and extending from an end of the anchor;

an inner layer, the liner being mounted over the inner layer, the inner element being spiral cut at a distal end; and an outer layer extending over the liner and the anchor, the outer layer being retracted to expose the liner when the outer layer is moved proximally relative to the inner layer, the inner and outer layers extending beyond a distal end of the liner, the outer layer tapering distally and being flexible enough to expand over the tapered section when the outer layer is retracted relative to the inner layer.

* * * * *